US011401311B2

(12) United States Patent
Hirano et al.

(10) Patent No.: US 11,401,311 B2
(45) Date of Patent: Aug. 2, 2022

(54) RECOMBINANT ACTIVIN A PRECURSOR PROTEIN

(71) Applicant: AJINOMOTO CO., INC., Tokyo (JP)

(72) Inventors: Hiroto Hirano, Kawasaki (JP); Kenichiro Ito, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 17/025,242

(22) Filed: Sep. 18, 2020

(65) Prior Publication Data

US 2021/0017245 A1 Jan. 21, 2021

Related U.S. Application Data

(63) Continuation of application No. PCT/JP2019/011357, filed on Mar. 19, 2019.

(30) Foreign Application Priority Data

Mar. 22, 2018 (JP) ............................ JP2018-053947

(51) Int. Cl.
*C07K 14/495* (2006.01)
*C07K 14/46* (2006.01)

(52) U.S. Cl.
CPC .......... *C07K 14/495* (2013.01); *C07K 14/461* (2013.01)

(58) Field of Classification Search
None
See application file for complete search history.

(56) References Cited

U.S. PATENT DOCUMENTS 6,084,076 A 7/2000 Ejima et al.

FOREIGN PATENT DOCUMENTS

WO WO97/23638 A1 7/1997

OTHER PUBLICATIONS

Johnson, K.E., et al. 2016 Molecular and Cellular Endocrinology 422: 84-92. (Year: 2016).*
Wang, X., et al., "Structure and activation of pro-activin A," Nat. Commun. 2016;7(12052):1-11.
International Search Report and Written Opinion for PCT Patent App. No. PCT/JP2019/011357 (dated Jun. 18, 2019).

* cited by examiner

*Primary Examiner* — Marsha Tsay
(74) *Attorney, Agent, or Firm* — Cermak Nakajima & McGowan LLP

(57) ABSTRACT

Provided is a recombinant activin A precursor protein that has human activin A activity. Also provided is a novel method for producing human activin A. The present invention pertains to a recombinant activin A precursor protein that includes a human mature activin A sequence and a non-human activin A prodomain, wherein said recombinant activin A precursor protein is not a naturally occurring activin A precursor protein. The present invention also pertains to a method for producing a human activin A using the aforesaid recombinant activin A precursor protein.

17 Claims, 5 Drawing Sheets

Specification includes a Sequence Listing.

RECOMBINANT ACTIVIN A PRECURSOR PROTEIN

This application is a Continuation of, and claims priority under 35 U.S.C. § 120 to, International Application No. PCT/JP2019/011357, filed Mar. 19, 2019, and claims priority therethrough under 35 U.S.C. § 119 to Japanese Patent Application No. 2018-053947, filed Mar. 22, 2018, the entireties of which are incorporated by reference herein. Also, the Sequence Listing filed electronically herewith is hereby incorporated by reference (File name: 2020-09-18T_US-618_Seq_List; File size: 39 KB; Date recorded: Sep. 18, 2020).

TECHNICAL FIELD

The present invention relates to a recombinant activin A precursor protein, a method for producing human activin A using the same, and the like.

BACKGROUND ART

Proteins belonging to the TGF-β family contribute to the generation of living organisms, differentiation, adjustment of cell proliferation, and the like, and are also important as differentiating factors for undifferentiated cells. However, since these proteins have complicated disulfide bonds in the molecules, it is often the case that when these proteins are produced using *Escherichia coli* and the like, the proteins are not correctly folded and fail to reproduce the conformations, thus having no activity.

Activin A, which belongs to the TGF-β family, is a protein present as a homodimer in which two polypeptide chains are linked by multiple disulfide bonds. Activin A is expressed as a precursor (also referred to as pro-activin A), and the precursor has a mature activin A sequence and an activin A prodomain. It is known that as a precursor (pro-activin A), activin A has no activity, and by cleaving the prodomain portion, the mature activin A sequence is released and forms active activin A having a predetermined conformation (Xuelu Wang et al., Nature Communications, 2016, 7:12052). In addition, activin A is known to induce iPS cells to differentiate into definitive endoderm.

Although there have been attempts to produce human activin A by utilizing microorganisms such as *Escherichia coli* as hosts, human activin A thus produced is often not correctly folded, and fails to reproduce the conformation, thus having no activity. For this reason, it is difficult to produce human activin A having activity by utilizing microorganisms such as *Escherichia coli* as hosts.

A method for refolding the conformation of human activin A having no activity into the conformation of human activin A having activity has been known (International Publication No. 97/23638). However, since it is necessary to conduct the refolding method separately after producing human activin A utilizing microorganisms such as *Escherichia coli* as hosts, this method cannot be said to be simple and convenient.

In addition, as described above, it is known that as the precursor, activin A has no activity, and by cleaving the prodomain portion, the mature activin A sequence is released and forms active activin A. An activin A precursor protein having activity while having the prodomain portion has not been reported to date.

SUMMARY OF INVENTION

An aspect of the present invention is to provide a novel method for producing human activin A.

In addition, another aspect of the present invention is to provide a recombinant activin A precursor protein for use in the novel method for producing human activin A.

Furthermore, still another aspect of the present invention is to provide a recombinant activin A precursor protein having human activin A activity.

The present inventors attempted to produce human activin A by using plant cells. However, the accumulation of target human activin A was not confirmed when merely expressing a gene encoding only a human mature activin A sequence forming human activin A having activity in plant cells. Even for animals that express activin A, it has been originally impossible to express only the active type (mature activin sequence), and it was found to be significantly difficult to express only the active type (mature activin sequence).

As a result of earnest studies, the present inventors newly found that it is possible to produce human activin A having activity by expressing, in plant cells, not a gene encoding only a human mature activin A sequence, but a gene encoding a recombinant activin A precursor protein including a human mature activin A sequence and a non-human activin A prodomain to generate the recombinant activin A precursor protein, and subsequently cleaving the human mature activin A sequence from the recombinant activin A precursor protein.

In addition, the present inventors newly found that the recombinant activin A precursor protein including the human mature activin A sequence and the non-human activin A prodomain has human activin A activity by itself.

The present invention may include, for example, the following aspects:

It is an aspect of the present invention to provide a recombinant activin A precursor protein comprising a human mature activin A sequence; and a non-human activin A prodomain, wherein the recombinant activin A precursor protein does not naturally occur.

It is a further aspect of the present invention to provide the recombinant activin A precursor protein as described above, wherein the non-human activin A prodomain is naturally derived from an amphibian, a reptile, or a fish.

It is a further aspect of the present invention to provide the recombinant activin A precursor protein as described above, wherein the non-human activin A prodomain is naturally derived from a fish.

It is a further aspect of the present invention to provide the recombinant activin A precursor protein as described above, wherein the activin A prodomain comprises a sequence having 90% or more identity with a sequence shown in SEQ ID NO: 1.

It is a further aspect of the present invention to provide the recombinant activin A precursor protein as described above, wherein the sequence having 90% or more identity with the sequence shown in SEQ ID NO: 1 is located at positions corresponding to positions 187 to 196 of a sequence shown in SEQ ID NO: 2.

It is a further aspect of the present invention to provide the recombinant activin A precursor protein as described above, wherein the non-human activin A prodomain has 90% or more identity with a sequence shown in SEQ ID NO: 2.

It is a further aspect of the present invention to provide the recombinant activin A precursor protein as described above, wherein the non-human activin A prodomain has 90% or more identity with a sequence represented by SEQ ID NO: 3.

It is a further aspect of the present invention to provide the recombinant activin A precursor protein as described above, wherein the non-human activin A prodomain has 90% or more identity with a sequence shown in SEQ ID NO: 4.

It is a further aspect of the present invention to provide the recombinant activin A precursor protein as described above, wherein the non-human activin A prodomain has 90% or more identity with a sequence shown in SEQ ID NO: 5.

It is a further aspect of the present invention to provide the recombinant activin A precursor protein as described above, wherein the non-human activin A prodomain has 90% or more identity with a sequence shown in SEQ ID NO: 6.

It is a further aspect of the present invention to provide the recombinant activin A precursor protein as described above comprising a sequence specifically cleavable by a protease between the human mature activin A sequence and the non-human activin A prodomain.

It is a further aspect of the present invention to provide a polynucleotide encoding the recombinant activin A precursor protein as described above.

It is a further aspect of the present invention to provide a recombinant vector comprising the polynucleotide as described above.

It is a further aspect of the present invention to provide a transformant comprising the polynucleotide as described above or the recombinant vector as described above.

It is a further aspect of the present invention to provide a method for producing the recombinant activin A precursor protein as described above comprising a step of, in a plant cell into which the polynucleotide as described above or the recombinant vector as described above has been introduced, or in a plant comprising the plant cell, expressing the polynucleotide.

It is a further aspect of the present invention to provide a method for producing human activin A comprising the steps of in a plant cell into which a polynucleotide encoding a recombinant activin A precursor protein as described above or a recombinant vector comprising the polynucleotide has been introduced, or in a plant comprising the plant cell, expressing the polynucleotide to generate the recombinant activin A precursor protein; and treating the recombinant activin A precursor protein with the protease.

In one embodiment, a recombinant activin A precursor protein having human activin A activity is provided. "Human activin A activity" as used herein may mean the property of activating the Smad protein, which is a signaling factor, and/or the property of inducing iPS cells to differentiate into definitive endoderm.

In one embodiment, a novel method for producing human activin A can be provided. One aspect of this producing method may be simpler than the conventional methods. One aspect of this producing method may be more economical than the conventional methods. Moreover, one aspect of this producing method may have a higher production efficiency than the conventional methods.

The producing method as described herein makes it possible to produce human activin A that maintains human activin A activity, unlike the producing methods utilizing microorganisms such as *Escherichia coli.*

BRIEF DESCRIPTION OF DRAWINGS

FIG. 4 shows, in order from the left, activin A produced by R&D systems (R&D ActA); a recombinant activin A precursor protein including an African clawed frog-derived prodomain (Xeno-Pro ActA); a recombinant activin A precursor protein including an African clawed frog-derived prodomain+furinΔC (Xeno-Pro ActA/Furin); a recombinant activin A precursor protein including a green sea turtle-derived prodomain (Umi-Pro ActA); a recombinant activin A precursor protein including a green sea turtle-derived prodomain+furinΔC (Umi-Pro ActA/Furin); a recombinant activin A precursor protein including a zebrafish-derived prodomain (Zeb-Pro ActA); and a sample to which no activin A was added (Mock). The horizontal axis in R&D ActA indicates the concentration (ng/mL), and the horizontal axis in those other than R&D ActA and Mock indicates the dilution ratio of the purified protein extract to the medium, or the dilution ratio of the partially purified mixed solution obtained by mixing the purified furinΔC and the recombinant activin A precursor protein to the medium. The vertical axis indicates a relative Smad activity.

FIG. 5 shows, in order from the left, activin A produced by R&D systems (R&D ActA); a recombinant activin A precursor protein including a zebrafish-derived prodomain (Zeb-Pro ActA); a recombinant activin A precursor protein including a channel catfish-derived prodomain (Amenama-Pro ActA); a recombinant activin A precursor protein including a coelacanth-derived prodomain (Latime-Pro ActA); and a sample to which no activin A was added (Mock). The horizontal axis in R&D ActA indicates the concentration (ng/mL), and the horizontal axis in those other than R&D ActA and Mock indicates the dilution ratio of the purified protein extract to the medium. The vertical axis indicates a relative Smad activity.

DESCRIPTION OF EMBODIMENTS

Recombinant Activin A Precursor Protein

Figure 1:
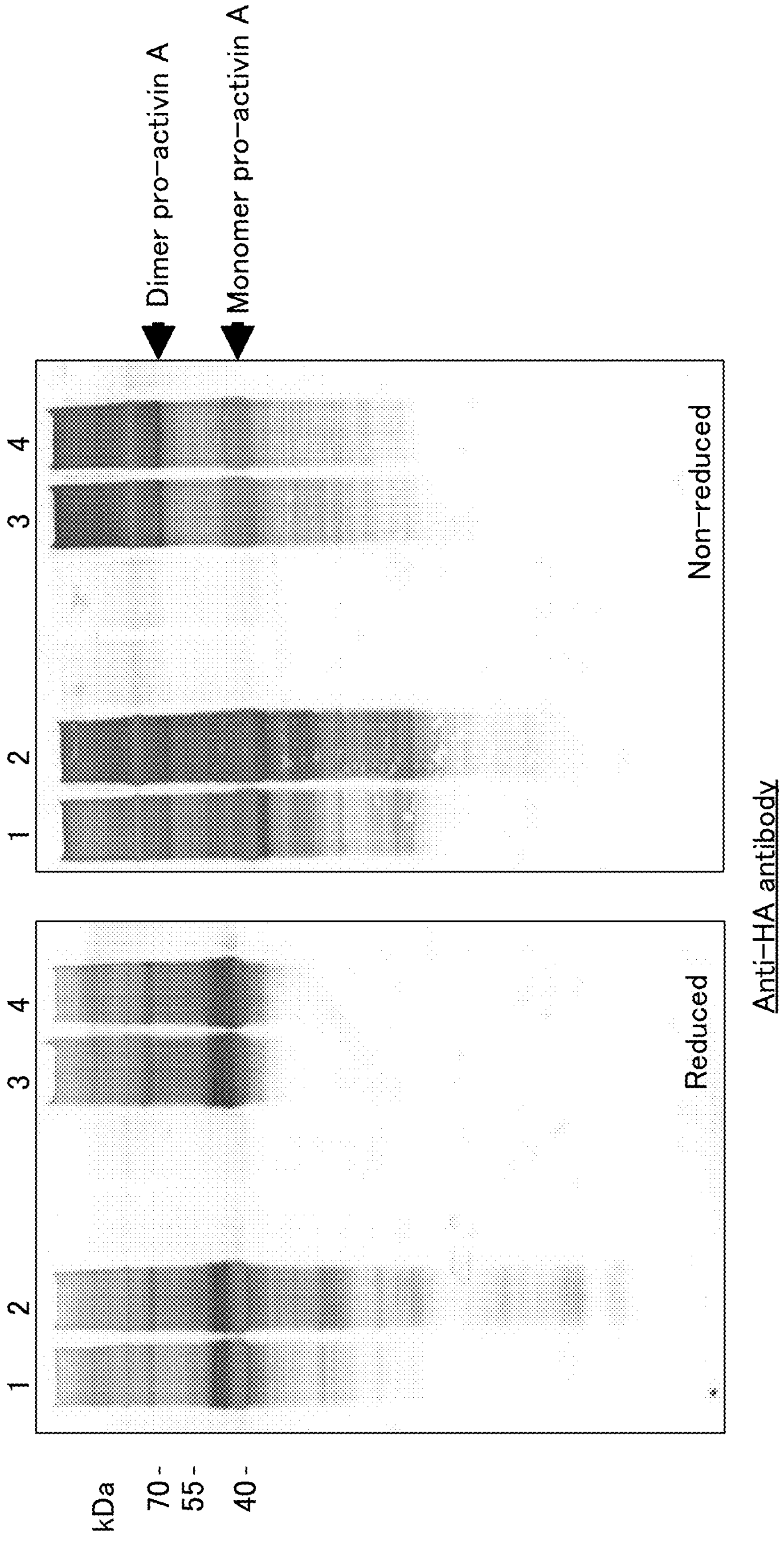
FIG. 1 illustrates photographs showing results of the western blotting with an anti-HA antibody. Lanes 1 and 2 show the results using extracts obtained by expressing a recombinant activin A precursor protein including a green sea turtle-derived prodomain in *Nicotiana benthamiana* and extracting proteins at the 4th day and the 5th day, respectively. Lanes 3 and 4 show the results using extracts obtained by expressing a recombinant activin A precursor protein including a zebrafish-derived prodomain in *Nicotiana benthamiana* and extracting proteins at the 4th day and the 5th day, respectively.

An embodiment as described herein relates to a recombinant activin A precursor protein (hereinafter, sometimes referred to as the "recombinant activin A precursor protein of the present invention") including a human mature activin A sequence and a non-human activin A prodomain, wherein the recombinant activin A precursor protein is not a naturally occurring activin A precursor protein. In one aspect, the recombinant activin A precursor protein including a human mature activin A sequence and a non-human activin A prodomain may be used in a novel method for producing human activin A. In addition, it is known that the precursor protein of activin A including a non-human activin A prodomain has no human activin A activity; however, in one aspect, it is possible that the recombinant activin A precursor protein including: a human mature activin A sequence; and a non-human activin A prodomain has human activin A activity.

"Human mature activin A sequence" as used herein means the C-terminus amino acid sequence of activin A which has been cleaved from the precursor protein of activin A (pro-activin A) expressed in a human living organism and which actually has activity. The "human mature activin A sequence" is a sequence made of 116 amino acids at positions 304 to 419 in a sequence shown in SEQ ID NO: 8, which will be described herein.

"Non-human activin A prodomain" as used herein means an inactive N-terminus amino acid sequence included in a precursor protein of activin A (pro-activin A) expressed in a living organism other than the human by the living organism, and is an amino acid sequence of a part excluding the C-terminus amino acid sequence of activin A which actually has activity and a protease recognition sequence adjacent to the N-terminus side of the C-terminus amino acid sequence.

In one embodiment, the non-human activin A prodomain is an activin A prodomain of, that is, naturally occurring or derived from, a bird, an amphibian, a reptile, a fish, or a mammal other than a human, and that derived from an amphibian, a reptile, or a fish is a particular example. Although examples of the non-human activin A prodomain will be given below, the non-human activin A prodomain is not limited to only the examples given below.

The activin A prodomain of a fish can include a sequence having an amino acid sequence identity of 90% or more with an amino acid sequence of DTRRSGWHTL (SEQ ID NO: 1), and another example includes a sequence having an amino acid sequence identity of 90% or more with the sequence shown in SEQ ID NO: 1 at positions corresponding to positions 187 to 196 of a sequence shown in SEQ ID NO: 2, which will be described herein, but is not limited to these.

For example, the activin A prodomain of a fish includes those selected from the amino acid sequences of the activin A prodomains derived from or native to the following living organisms: zebrafish (*Danio rerio*), channel catfish (*Ictalurus punctatus*), coelacanth (*Latimeria chalumnae*), *Sinocyclocheilus rhinocerous, Sinocyclocheilus anshuiensis, Sinocyclocheilus grahami*, common carp (*Cyprinus carpio*), goldfish (*Carassius auratus*), grass carp (*Ctenopharyngodon idellus*), *Pundamilia nyererei*, Mexican tetra (*Astyanax mexicanus*), *Maylandia* zebra, Japanese rice fish (*Oryzias latipes*), platy (*Xiphophorus maculatus*), guppy (*Poecilia reticulata*), sailfin molly (*Poecilia latipinna*), amazon molly (*Poecilia formosa*), Atlantic molly (*Poecilia mexicana*), barramundi (*Lates calcarifer*), Atlantic salmon (*Salmo salar*), northern pike (*Esox lucius*), Asian arowana (*Scleropages formosus*), *Maylandia* Zebra, *Haplochromis* (*Haplochromis burutoni*), yellow croaker (*Larimichthys crocea*), mangrove killifish (*Kryptolebias marmoratus*), spiny chromis (*Acanthochromis polyacanthus*), yellowtail amberjack (*Seriola lalandi dorsalis*), spotted gar (*Lepisosteus oculatus*), silver salmon (*Oncorhynchus kisutch*), Atlantic herring (*Clupea harengus*), walking catfish (*Clavas batrachus*), piranha (*Pygocentrus nattereri*), rainbow trout (*Oncorhynchus mykiss*), ocellaris clownfish (*Amphiprion ocellaris*), bicolor damselfish (*Stegastes partitus*), greater amberjack (*Seriola dumerili*), Hong Kong catfish (*Clavas gariepinus*), tilapia (*Oreochromis niloticus*), annual killifish (*Austrofundulus limnaeus*), mummichog (*Fundulus heterochtus*), southern platyfish (*Xiphophorus maculatus*), *Neolamprologus brichardi*, wrasse (*Labrus bergyha*), and Asian swamp eel (*Monopterus albus*).

The activin A prodomain of a fish may be selected from the amino acid sequences of the activin A prodomains derived from or native to living organisms belonging to Cypriniformes, Silunformes, or Coelacanthiformes. In addition, the activin A prodomain of a fish may be selected from the amino acid sequences of the activin A prodomains derived from living organisms belonging to Cyprinidae, ktaluridae, or Latimeriidae, or may be selected from the amino acid sequences of the activin A prodomains derived from or native to living organisms belonging to *Danio, Ictalurus*, or *Latimeria.*

Throughout this specification, the expression "derived from" can be used interchangeably with "native to".

The non-human activin A prodomain may be one having an amino acid sequence identity of 90% or more, 95% or more, or 98% or more with the amino acid sequence of the activin A prodomain of a fish, and is not limited to the above-described examples.

The non-human activin A prodomain has an amino acid sequence identity of 90% or more, 95% or more, or 98% or more with the amino acid sequence (SEQ ID NO: 2) of the activin A prodomain derived from zebrafish. The non-human activin A prodomain can include the amino acid sequence of the activin A prodomain derived from zebrafish. The non-human activin A prodomain can be made of the amino acid sequence of the activin A prodomain derived from zebrafish.

The amino acid sequence identity herein can be calculated using a publicly-known analysis tool, and for example, can be calculated using the identity algorithm BLAST (Basic local alignment search tool) of the National Center for Biotechnology Information (NCBI). In addition, for the calculation of the amino acid sequence identity, parameters of the default (initial setting) in the analysis tool may be used.

The non-human activin A prodomain has an amino acid sequence identity of 90% or more, 95% or more, or 98% or more with the amino acid sequence (SEQ ID NO: 3) of the activin A prodomain derived from channel catfish. The non-human activin A prodomain can include the amino acid sequence of the activin A prodomain derived from channel catfish. The non-human activin A prodomain can be made of the amino acid sequence of the activin A prodomain derived from channel catfish.

The non-human activin A prodomain has an amino acid sequence identity of 90% or more, 95% or more, or 98% or more with the amino acid sequence (SEQ ID NO: 4) of the activin A prodomain derived from coelacanth. The non-human activin A prodomain can include the amino acid sequence of the activin A prodomain derived from coelacanth. The non-human activin A prodomain can be made of the amino acid sequence of the activin A prodomain derived from coelacanth.

For example, the activin A prodomain of an amphibian includes those selected from the amino acid sequences of the activin A prodomains derived from the following living organism: African clawed frog (*Xenopus laevis*), Japanese fire belly newt (*Cynops pyrrhogaster*), western clawed frog (*Xenopus tropicalis*), *Nanorana parkeri*, common coqui (*Eleutherodactylus coqui*), and American bullfrog (*Lithobates catesbeiana*).

The activin A prodomain of an amphibian may be selected from the amino acid sequences of the activin A prodomains derived from living organisms belonging to *Anura*. In addition, the activin A prodomain of an amphibian may be selected from amino acid sequences of the activin A prodomains derived from living organisms belonging to Pipidae, or may be selected from amino acid sequences of the activin A prodomains derived from living organisms belonging to *Xenopus*.

The non-human activin A prodomain may be one having an amino acid sequence identity of 90% or more, 95% or more, or 98% or more with the amino acid sequence of the activin A prodomain of an amphibian, and is not limited to the above-described examples.

The non-human activin A prodomain has an amino acid sequence identity of 90% or more, 95% or more, or 98% or more with the amino acid sequence (SEQ ID NO: 5) of the activin A prodomain derived from African clawed frog. The non-human activin A prodomain can include the amino acid sequence of the activin A prodomain derived from African clawed frog. The non-human activin A prodomain can be made of the amino acid sequence of the activin A prodomain derived from African clawed frog.

For example, the activin A prodomain of a reptile includes those selected from amino acid sequence of activin A prodomain derived from the following living organisms: green sea turtle (*Chelonia mydas*), Indian *Python* (*Python molurus*), green anole (*Anolis carolinensis*), central bearded dragon (*Pogona vitticeps*), Japanese gecko (*Gekko japonicus*), king cobra (*Ophiophagus hannah*), garter snake (*Thamnophis sirtalis*), brown spotted pit viper (*Protobothrops mucrosquamatus*), painted turtle (*Chrysemys picta*), Chinese *Alligator* (*Alligator sinensis*), Indian gavial (*Gavialis gangeticus*), and American *Alligator* (*Alligator mississippiensis*).

The activin A prodomain of a reptile may be selected from the amino acid sequences of the activin A prodomains derived from living organisms belonging to Testudines. In addition, the activin A prodomain of a reptile may be selected from the amino acid sequences of the activin A prodomains derived from living organisms belonging to Cheloniidae, or may be selected from the amino acid sequences of the activin A prodomains derived from living organisms belonging to *Chelonia*.

The non-human activin A prodomain may be one having an amino acid sequence identity of 90% or more, 95% or more, or 98% or more with the amino acid sequence of the activin A prodomain of a reptile, and is not limited to the above-described examples.

The non-human activin A prodomain has an amino acid sequence identity of 90% or more, 95% or more, or 98% or more with the amino acid sequence (SEQ ID NO: 6) of the activin A prodomain derived from green sea turtle. The non-human activin A prodomain can include the amino acid sequence of the activin A prodomain derived from green sea turtle. The non-human activin A prodomain can be made of the amino acid sequence of the activin A prodomain derived from green sea turtle.

The phrase "not a naturally occurring activin A precursor protein" or "does not naturally occur" as used herein means that the recombinant activin A precursor protein is different in amino acid sequence from the precursor proteins of activin A (pro-activin A) produced by the expression of genes of natural living organisms whose genes are not modified. In other words, the recombinant activin A precursor protein including a human mature activin A sequence and a non-human activin A prodomain as described herein is different in amino acid sequence from the precursor proteins of activin A produced by the expression of genes of natural living organisms whose genes are not modified.

For example, some mature activin A sequences in primates such as monkeys have the same sequence as the mature activin A sequence of the human. Hence, a activin A precursor protein including the mature activin A sequence of a monkey and the activin A prodomain of the monkey is deemed to be the same as the activin A precursor protein including the mature activin A sequence of the human and the activin A prodomain of the monkey, and the phrase "not a naturally occurring activin A precursor protein" or "does not naturally occur" as used herein is intended to mean that such an activin A precursor protein is excluded from the scope of the present invention.

In the recombinant activin A precursor protein including a human mature activin A sequence and a non-human activin A prodomain, the human mature activin A sequence can be located closer to the C-terminus than the non-human activin A prodomain. In addition, the recombinant activin A precursor protein can include a sequence specifically cleavable by a protease between the human mature activin A sequence and the non-human activin A prodomain. The sequence specifically cleavable by a protease can be adjacent to the human mature activin A sequence and the non-human activin A prodomain and can be adjacent to the C-terminus side of the non-human activin A prodomain and to the N-terminus side of the human mature activin A sequence.

The sequence specifically cleavable by a protease includes a furin recognition sequence, a TEV protease recognition sequence, an HRV 3C protease recognition sequence, a thrombin recognition sequence, a factor Xa recognition sequence, or an enterokinase recognition sequence, and the like, but the sequence specifically cleavable by a protease is not limited to these. The sequence specifically cleavable by a protease can be one that can be cleaved on the C-terminus side of the sequence, and also can be a furin recognition sequence. The furin recognition sequence is a sequence that generally has arginine at the C-terminus, or has lysine at the C-terminus in some cases, and in which the C-terminus side can be cleaved by furin. For example, a standard furin recognition sequence can be expressed by an amino acid sequence represented by R-X-(K/R)-R (X is any amino acid), but the furin recognition sequence is not limited to this.

The recombinant activin A precursor protein may include a desired tag bound in a genetically engineered manner, for example, the His tag, the HA tag, the FLAG tag, the Myc tag, or the like. As the tag, a tag that does not affect the conformation of the activin A precursor protein can be used, and a tag formed of 5 to 15 amino-acid residues is another example. In the case where the recombinant activin A precursor protein includes a tag, the tag can be located on the N-terminus side of the non-human activin A prodomain.

Polynucleotide that Encodes Recombinant Pro-Activin A Protein

One embodiment as described herein relates to a polynucleotide encoding the recombinant activin A precursor protein. The polynucleotide can be synthesized by those skilled in the art based on the common technical knowledge.

The polynucleotide encoding the recombinant activin A precursor protein may include a nucleic acid sequence encoding any signal sequence bounded to the N-terminus side in a genetically engineered manner. The signal sequence can be an endoplasmic reticulum insertion signal sequence, and an endoplasmic reticulum insertion signal sequence known by those skilled in the art such as one derived from thale cress may be used.

When the recombinant activin A precursor protein includes a tag on the N-terminus side of the non-human activin A prodomain, the polynucleotide encoding the recombinant activin A precursor protein can include a nucleic acid sequence encoding the signal sequence the side closer to the N-terminus than the nucleic acid sequence encoding the tag.

Recombinant Vector

One embodiment as described herein relates to a recombinant vector including a polynucleotide encoding the recombinant activin A precursor protein as described herein. The usable vector may be one that can functionally insert the polynucleotide and can carry the different nucleic acid fragment into a host cell to allow the fragment to be replicated or expressed in the host cell, and includes, for example, plasmids, phages, cosmids, and viruses. The vector can be appropriately selected by those skilled in the art depending on the type of an assumed host cell.

The host cell includes, for example, plant cells, insect cells, fungus cells (yeast), prokaryotic cells (*Escherichia coli*), animal cells (CHO). Among these, since plant cells are assumed as the host cell, the vector can be an expression vector for plant cells, such as pRI 201 DNA series (TAKARA BIO Inc.), but is not limited to these. An appropriate vector may be selected and used depending on the type of a plant cell.

Transformant

One embodiment as described herein relates to a transformant including a polynucleotide encoding the recombinant activin A precursor protein, or a transformant including a recombinant vector including a polynucleotide encoding the recombinant activin A precursor protein.

"Transformant" as used herein means a host or host cell in which a different nucleic acid fragment has been introduced. The nucleic acid fragment for transformation, that is, the polynucleotide encoding the recombinant activin A precursor protein may be incorporated into the genome of the host or host cell or may not be incorporated. For example, the nucleic acid fragment for transformation may be maintained in an episome or a plasmid. The gene may be appropriately introduced by those skilled in the art based on the technical common knowledge. For example, the transformant can be a plant cell or a plant, and as a method for introducing a gene into a plant cell or a plant, the agroinfiltration method, the plant virus vector method, and the like are known.

Method for Producing Recombinant Pro-Activin A Protein

One embodiment as described herein is a method for producing the recombinant activin A precursor protein. The method for producing a recombinant activin A precursor protein includes a step of, in a plant cell into which the polynucleotide encoding the recombinant activin A precursor protein or a recombinant vector including the polynucleotide has been introduced, or in a plant including the plant cell, expressing a polynucleotide. This allows the plant cell or the plant to produce the target recombinant activin A precursor protein.

In the method for producing a recombinant activin A precursor protein, the expression of the polynucleotide may be transient or stable in a plant cell or a plant. The culture conditions for the plant cell may be selected by those skilled in the art as appropriate based on the common technical knowledge in accordance with the type of the plant cell chosen. For example, the culture medium and the conditions such as the temperature, the humidity, and the concentration of carbon dioxide, and the like of the environment where the culture is to be conducted are not particularly limited as long as the culture medium and the conditions are suitable for each cell, and may be selected from a conventionally known culture medium and conditions. The cultivating conditions for a plant can also be selected by those skilled in the art as appropriate based on the common technical knowledge in accordance with the type of the plant chosen.

The plant used for the method for producing a recombinant activin A precursor protein is not particularly limited, but can be a plant that can be infected with *Agrobacterium*. For example, the plant may be a dicot or may be a monocot. The dicot includes Solanaceae plants such as tobacco, tomato, and potato, Brassicaceae plants such as thale cress, rapeseed, broccoli, and cabbage, Asteraceae plants such as crown daisy and lettuce, Rosaceae plants such as strawberry, Japanese apricot, apple, and peach, Fabaceae plants such as soybean, peanut, and mung bean, Apiaceae plants such as carrot and celery, Cucurbitaceae plants such as melon, watermelon, and cucumber, Convolvulaceae plants such as Japanese morning glory and sweet potato, Chenopodiaceae plants such as spinach, quinoa, and sugar beet, and the like. The monocot includes Poaceae plants such as rice, wheat, barley, and corn, Liliaceae plants such as garlic, onion, and Welsh onion, and the like.

The plant used for the method for producing a recombinant activin A precursor protein can be a Solanaceae plant, and tobacco is another example. Tobacco includes, for example, *Nicotiana benthamiana, Nicotiana tabacum, Nicotiana rustica, Nicotiana tomentosifonnis, Nicotiana sylvestris*, and the like, and *Nicotiana benthamiana* is a particular example.

The plant cell used for the method for producing a recombinant activin A precursor protein is also not particularly limited, and cells of the above-described plants may be used.

In the method for producing a recombinant activin A precursor protein, when the recombinant activin A precursor protein includes a sequence specifically cleavable by a protease between the human mature activin A sequence and the non-human activin A prodomain, the sequence specifically cleavable by a protease is one that is not cleaved by a protease present inside the plant cell to be used as the host cell.

The method for producing a recombinant activin A precursor protein may further include a step of extracting, from the plant cell or the plant, a recombinant activin A precursor protein generated in the plant cell or the plant. For example, the protein can be extracted from the plant cell by breaking the tissue using something like a mixer or a mortar with water or a buffer. Such an extracting step can be conducted by those skilled in the art as appropriate based on the common technical knowledge.

The method for producing a recombinant activin A precursor protein may further include a step of purifying the extract containing the recombinant activin A precursor protein extracted from the plant cell or the plant. For example, it is possible to add an epitope tag to the recombinant protein in advance, and purify the recombinant protein by a purifying method according to the added epitope. The epitope tag includes the histidine tag, the HA tag, the GST tag, the MBP tag, the MYC tag, the DYKDDDDK [SEQ ID NO:17] tag, the streptavidin tag, and the like. Such a purifying step can be conducted by those skilled in the art as appropriate based on the common technical knowledge.

Method for Producing Human Activin A

One embodiment as described herein is a method for producing human activin A (hereinafter, sometimes referred to as the "method for producing human activin A of the present invention"), and human activin A produced by this producing method may have human activin A activity.

The method for producing human activin A includes at least the following two steps:

1. In a plant cell into which a polynucleotide encoding the recombinant activin A precursor protein or a recombinant vector including the polynucleotide has been introduced, or in a plant including the plant cell, expressing the polynucleotide to generate the recombinant activin A precursor protein. Here, the recombinant activin A precursor protein includes a human mature activin A sequence and a non-human activin A prodomain and also includes a sequence specifically cleavable by a protease between the human mature activin A sequence and the non-human activin A prodomain; and 2. Treating the recombinant activin A precursor protein with the protease.

In the method for producing human activin A, the recombinant activin A precursor protein is of an aspect that includes a human mature activin A sequence and a non-human activin A prodomain and also includes a sequence specifically cleavable by a protease between the human mature activin A sequence and the non-human activin A prodomain, among the above-described recombinant activin A precursor protein. The sequence specifically cleavable by a protease can be adjacent to the human mature activin A sequence and the non-human activin A prodomain, and can be adjacent to the C-terminus side of the non-human activin A prodomain and the N-terminus side of the human mature activin A sequence.

The sequence specifically cleavable by a protease includes a furin recognition sequence, a TEV protease recognition sequence, an HRV 3C protease recognition sequence, a thrombin recognition sequence, a factor Xa recognition sequence, or an enterokinase recognition sequence, and the like, but the sequence specifically cleavable by a protease is not limited to these. The sequence specifically cleavable by a protease can be one that can be cleaved on the C-terminus side of the sequence, and can be a furin recognition sequence. The furin recognition sequence is a sequence that generally has arginine at the C-terminus (has lysine at the C-terminus in some cases), and in which the C-terminus side can be cleaved by furin. For example, a standard furin recognition sequence can be expressed by an amino acid sequence represented by R-X-(K/R)-R (X is any amino acid), but the furin recognition sequence is not limited to this.

In the method for producing human activin A, the expression of the polynucleotide may be transient or stable in a plant cell or a plant. The culture conditions for the plant cell may be selected by those skilled in the art as appropriate based on the common technical knowledge in accordance with the type of the plant cell used. For example, the culture medium and the conditions such as the temperature, the humidity, and the concentration of carbon dioxide, and the like of the environment where the culture is to be conducted are not particularly limited as long as the culture medium and the conditions are suitable for each cell, and may be selected from a conventionally known culture medium and conditions. The cultivating conditions for a plant can also be appropriately selected by those skilled in the art based on the common technical knowledge in accordance with the type of the plant used.

The plant used for the method for producing human activin A is not particularly limited, but can be a plant that can be infected with *Agrobacterium*. For example, the plant may be a dicot or may be a monocot. The dicot includes Solanaceae plants such as tobacco, tomato, and potato, Brassicaceae plants such as thale cress, rapeseed, broccoli, and cabbage, Asteraceae plants such as crown daisy and lettuce, Rosaceae plants such as strawberry, Japanese apricot, apple, and peach, Fabaceae plants such as soybean, peanut, and mung bean, plants such as carrot and celery, Cucurbitaceae plants such as melon, watermelon, and cucumber, Convolvulaceae plants such as Japanese morning glory and sweet potato, Chenopodiaceae plants such as spinach, quinoa, and sugar beet, and the like. The monocot includes Poaceae plants such as rice, wheat, barley, and corn, Liliaceae plants such as garlic, onion, and Welsh onion, and the like.

The plant used for the method for producing a recombinant activin A precursor protein can be a Solanaceae plant, or tobacco. Tobacco includes, for example, *Nicotiana benthamiana, Nicotiana tabacum, Nicotiana rustica, Nicotiana tomentosifonnis, Nicotiana sylvestris*, and the like, and *Nicotiana benthamiana* is a particular example.

The plant cell used for the method for producing a recombinant activin A precursor protein is also not particularly limited, and cells of the above-described plants may be used.

In the method for producing human activin A, a human mature activin A sequence is cleaved by treating the recombinant activin A precursor protein generated in the plant cell or in the plant with the protease. The human mature activin A sequence itself forms human activin A, and human activin A produced by the method for producing human activin A in this manner can maintain its activity.

The protease that can be used in the method for producing human activin A includes the furin protease, the TEV protease, the HRV 3C protease, the thrombin, the factor Xa, or the enterokinase, and the like, but is not limited to these. The protease can be one that cleaves the C-terminus of the recognition sequence, and can be the furin protease. Note that although the furin protease is of lipid-raft type and naturally an insoluble protease, there is a report that the furin protease was converted into secreted soluble type by deleting the lipid-raft region using an insect cell (Bravo, D. a., Gleason, J. B., Sanchez, R. I., Roth, R. a. & Fuller, R. S. Accurate and efficient cleavage of the human insulin proreceptor by the human proprotein-processing protease furin. Characterization and kinetic parameters using the purified, secreted soluble protease expressed by a recombinant baculovirus. J. Biol. Chem. 269, 25830-25837 (1994), the contents of which are incorporated herein by reference), and it is possible to use a furin protease obtained by deleting the lipid-raft region present at the C-terminus of such furin protease in the method for producing human activin A.

The treatment with the protease may be conducted in a plant cell or a plant in which the recombinant activin A precursor protein has been generated. In this case, the protease may be a protease that is spontaneously present in a plant cell or in a plant, or a protease that is not spontaneously present in a plant cell or in a plant and may be expressed in a plant cell or in a plant by transformation using gene transfer. Such transfer of a gene into a plant cell or a plant can be appropriately conducted by those skilled in the art based on the common technical knowledge, and can be conducted by a method such as the agroinfiltration method or the plant virus vector method.

In addition, the treatment with the protease may be conducted outside a plant cell or a plant in which the recombinant activin A precursor protein has been generated. In this case, the protease may be a commercially-available protease or a protease prepared separately from the recombinant activin A precursor protein. For example, a furin protease obtained by deleting the lipid-raft region present at the C-terminus of a furin protease results in a secreted soluble type, and it is possible to react the furin protease with the recombinant activin A precursor protein outside a plant cell or a plant by preparing this furin protease separately from the recombinant activin A precursor protein and using the furin protease.

The method for producing human activin A may further include a step of extracting, from the plant cell or the plant, a recombinant activin A precursor protein generated in the plant cell or the plant. For example, the protein can be extracted from the plant cell by breaking the tissue using something like a mixer or a mortar with water or a buffer. Such an extracting step can be conducted by those skilled in the art as appropriate based on the common technical knowledge. This extracting step is conducted before the step of treating the recombinant activin A precursor protein with the protease.

The method for producing human activin A may further include a step of purifying the extract containing the recombinant activin A precursor protein extracted from the plant cell or the plant. For example, it is possible to add an epitope tag to the recombinant protein in advance, and purify the recombinant protein by a purifying method according to the added epitope. The epitope tag includes the histidine tag, the HA tag, the GST tag, the MBP tag, the MYC tag, the DYKDDDDK [SEQ ID NO:17] tag, or the streptavidin tag, and the like. Such a purifying step can be appropriately conducted by those skilled in the art based on the common technical knowledge. This purifying step is conducted before the step of treating the recombinant activin A precursor protein with the protease.

When the step of treating the recombinant activin A precursor protein with the protease has been conducted in a plant cell or in a plant, the method for producing human activin A may further include a step of extracting, from the plant cell or the plant, human activin A generated in the plant cell or the plant after the treating step. For example, the protein can be extracted from the plant cell by breaking the tissue using something like a mixer or a mortar with water or a buffer. Such an extracting step can be appropriately conducted by those skilled in the art based on the common technical knowledge.

The method for producing human activin A may further include a step of purifying the extract containing the human activin A extracted from the plant cell or the plant. For example, it is possible to add an epitope tag to the recombinant protein in advance, and purify the recombinant protein by a purifying method according to the added epitope. The epitope tag includes the histidine tag, the HA tag, the GST tag, the MBP tag, the MYC tag, the DYKDDDDK [SEQ ID NO:17] tag, or the streptavidin tag, and the like. Such a purifying step can be appropriately conducted by those skilled in the art based on the common technical knowledge.

EXAMPLES

Hereinafter, the present invention will be described in further detail with reference to specific Examples. However, the scope of the present invention is not limited to these Examples.

Materials and Method

1. Plant and its Cultivation Method

As the plant, tobacco (cultivar: *Nicotiana benthamiana*) was chosen. A cultivation soil was prepared by mixing Kumiai Nippi Engei Baido No. 1 and vermiculite in 1:1, and the cultivation soil thus prepared was put into a plug tray. Tobacco seeds were sowed on the plug tray, were cultivated for about 4 weeks, and were then transplanted into a No. 3 vinyl pot. For agroinfiltration, the plant in the second to third week after the transplantation in the vinyl pot was used. The cultivation was conducted at a light intensity of about 70 $\mu mol\ m^{-2}\ s^{-1}$ before the agroinfiltration (in the lower stage of the Biotron B room), and at a light intensity of about 150 $\mu mol\ m^{-2}\ s^{-1}$ after the agroinfiltration (in the upper stage of the Biotron B room).

2. Construction of Plasmid Vector and Artificial Gene Synthesis

Various insert DNAs, which were artificial genes, were inserted between the NdeI site immediately below the AtADH 5' UTR and the SalI site further downstream of the AtADH 5' UTR using the pRI201-AN vector (TAKARA BIO Inc.). The Gibson Assembly (Registered Trademark) Master Mix was used for the insertion of the insert DNAs.

The artificial genes were synthesized utilizing the GeneArt (Registered Trademark) Strings™ DNA Fragments service of Thermo Fisher Scientific. The synthesized genes were optimized in conformity with the frequency of codon occurrence of *Nicotiana benthamiana* using the GeneArt (Registered Trademark) GeneOptimizer (Registered Trademark) provided by Thermo Fisher Scientific.

The chosen artificial genes are shown in Table 1.

TABLE 1

| Description of Sequence | SEQ ID NO: |
|---|---|
| (ABC-SP)-(His tag)-(HA tag)-(zebrafish Pro-domain)-(Furin)-(human activin A) | SEQ ID NOs: 7, 8 |
| (ABC-SP)-(His tag)-(HA tag)-(channel catfish Pro-domain)-(Furin)-(human activin A) | SEQ ID NOs: 9, 10 |
| (ABC-SP)-(His tag)-(HA tag)-(coelacanth Pro-domain)-(Furin)-(human activin A) | SEQ ID NOs: 11, 12 |
| (ABC-SP)-(His tag)-(HA tag)-(African clawed frog Pro-domain)-(Furin)-(human activin A) | SEQ ID NOs: 13, 14 |
| (ABC-SP)-(His tag)-(green sea turtle Pro-domain)-(Furin)-(human activin A) | SEQ ID NOs: 15, 16 |

ABC-SP: endoplasmic reticulum insertion signal peptide derived from *Arabidopsis* basic chitinase Zebrafish Pro-domain: the activin A prodomain derived from zebrafish Channel catfish Pro-domain: the activin A prodomain derived from channel catfish Coelacanth Pro-domain: the activin A prodomain derived from coelacanth African clawed frog Pro-domain: the activin A prodomain derived from African clawed frog Green sea turtle Pro-domain: the activin A prodomain derived from green sea turtle Furin: the furin recognition sequence Human activin A: the human mature activin A sequence 3. Line and Transformation of *Escherichia coli* and *Agrobacterium*

The transformation was conducted using NEB (Registered Trademark) 10-beta strain (NEB) as *Escherichia coli* and LBA4404 strain (TAKARA BIO Inc.) as *Agrobacterium* in accordance with the protocols attached to the products. First, each plasmid vector was increased in *Escherichia coli* and was corrected, and subsequently each plasmid vector was introduced into *Agrobacterium*. For the culture of both *Escherichia coli* and *Agrobacterium*, an LB medium was used. *Escherichia coli* was cultured at 37° C. and *Agrobacterium* was cultured at 28° C.

4. Agroinfiltration

*Agrobacterium* holding each transgene was precultured in 3 ml of the LB medium at 28° C. overnight. The *Agrobacterium* suspension thus precultured was 10-fold diluted in the LB medium (1 ml of the agrosolution per 9 ml of the LB), and acetosyringone was added such that the final concentration became 100 μM, followed by main culture for 4 hours. The suspension subjected to the main culture was centrifuged at 4000 g for 5 minutes to collect bacterial cells. The pellets thus collected were suspended such that O.D.600=0.5 in a 10 mM IVIES (pH 5.5)+10 mM $MgCl_2$ solution, and acetosyringone was added such that the final concentration became 200 μM. The bacterial culture prepared in this manner was allowed to stand at room temperature 25° C. for 1 hour to 3 hours. Thereafter, a 1 ml needleless syringe was used. The syringe was brought into contact with the lower side of the tobacco leaf, then the upper side was pinched with fingers to cause the pressurized state, and the bacterial culture was injected into the leaf (agroinfiltration). After the agroinfiltration, cultivation was conducted at about 150 μmol $m^{-2}$ $s^{-1}$ (in the upper stage of the Biotron B room), and sampling was conducted between the 4th day and the 7th day after the inoculation.

5. Extraction of Protein

After the leaf subjected to the agroinfiltration was collected and the fresh weight was measured, a refrigerate extraction buffer was added in an amount 3 times the fresh weight, and the leaf in the raw or frozen at −80° C. was pulverized with a mortar. As the extraction buffer, a buffer obtained by adding NaCl to D-PBS such that the final concentration became 0.3 to 1 M, further adding Tween-20 in 0.5% to 1%, and adjusting pH to 7.4 was used. For use in metal affinity purification, imidazole was added such that the final concentration became 5 to 15 mM. In addition, commercially-available xTractor buffer (TAKARABIO Inc.) was also used as a buffer dedicated for the metal affinity purification.

6. Metal Affinity Purification

The protein extract was centrifuged with CR22G III centrifuge (Hitachi, Ltd.) at 18,000 g at 4° C. for 15 minutes to cause fragments of cells to precipitate, and the supernatant was recovered. The supernatant was transferred into himac 50 ml culture tube (Hitach, Ltd.) and centrifuged at 32,200 g at 4° C. for 30 to 60 minutes to cause finer fragments to precipitate, and the supernatant was recovered. An appropriate amount of TALON (Registered Trademark) Metal Affinity Resin (TAKARA BIO Inc.) or His60 Ni Superflow Resin (TAKARA BIO Inc.) was added to the supernatant, followed by shaking at 4° C. for 20 minutes or more to allow the Resin to adsorb the protein. Thereafter, the solution containing the Resin was transferred into a gravity column to recover the flow-through. Next, washing was conducted with a Washbuffer (D-PBS+final concentration 0.3 M NaCl, 15 mM imidazole, pH 7.4) in an amount 5 times the volume of the Resin. The elution was conducted by adding an elution buffer for Co resin (D-PBS+final concentration 0.3 M NaCl, 150 mM imidazole, 1 mM $CaCl_2$), pH 7.4) or an elution buffer for Ni resin (D-PBS+final concentration 0.3 M NaCl, 0.5 M imidazole, 1 mM $CaCl_2$), pH 8.0) in an amount twice the volume of the Resin to recover the eluate.

7. Western Blotting

The sample at the time of protein electrophoresis was heated at 100° C. for 3 minutes after a sample buffer solution (for SDS-PAGE, 6-time concentrated, containing a reducing agent) pH 6.0 (Nacalai Tesque, Inc.) was added. DTT or mercaptoethanol was used as a reducing agent. The sample for non-reduction was prepared by adding NuPAGE (Registered Trademark) 4×LDS Sample Buffer and treating at 70° C. for 10 minutes. As the polyacrylamide gel, e•PAGEL 15% (ATTO) was used to conduct electrophoresis. Thereafter, semi-dry blotting device PoweredBlot Ace (ATTO) was used to transfer the protein to the PVDF membrane. An antibody to the target protein was used as the primary antibody and an HRP antibody to each host animal was used as the secondary antibody. As the anti-activin antibody, a goat-derived polyclonal antibody (R&D systems, product code AF338) was used. As the anti-HA antibody, a rat monoclonal antibody Anti-HA High Affinity (Roche) was used. Detection was conducted by LAS-3000 (Fujifilm) using ECL™ Prime Western Blotting Detection Reagent of GE Healthcare.

The results of detection with the anti-HA antibody are illustrated in FIG. 1. Lanes 1 and 2 show the results using extracts obtained by expressing a recombinant activin A precursor protein including a green sea turtle-derived prodomain in *Nicotiana benthamiana* and extracting proteins at the 4th day and the 5th day, respectively. Lanes 3 and 4 show the results using extracts obtained by expressing a recombinant activin A precursor protein including a zebrafish-derived prodomain in *Nicotiana benthamiana* and extracting proteins at the 4th day and the 5th day, respectively.

As shown in FIG. 1, a band was detected near an estimated molecular weight (about 44 kDa) of a monomer pro-activin A in the reduced state and a band was detected near an estimated molecular weight (about 88 kDa) of a dimer pro-activin A in the non-reduced state. These suggested that the produced proteins were present in the state where the disulfide bond was able to be cleaved by the reducing agent and were folded in a state similar to the natural state.

Figure 2:
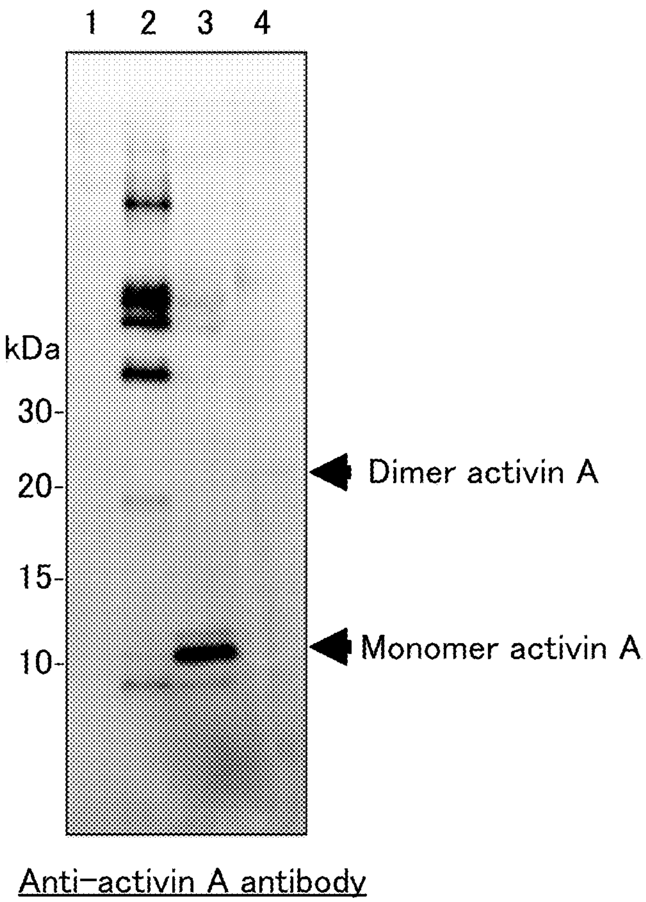
FIG. 2 illustrates a photograph showing results of the western blotting with an anti-activin A antibody. Lane 1 show a Co column-purified furinΔC protease; lane 2 shows a recombinant activin A precursor protein including a Co column-purified zebrafish-derived prodomain; lane 3 shows reducing conditions for a mixture of the Co column-purified furinΔC protease and the recombinant activin A precursor protein including the zebrafish-derived prodomain; and lane 4 shows non-reducing conditions for the mixture of the Co column-purified furinΔC protease and the recombinant activin A precursor protein including the zebrafish-derived prodomain.

The results of detection with the anti-activin A antibody are shown in FIG. 2. Lane 1 shows only the result obtained by deleting the lipid-raft region present at the C-terminus of the furin protease and adding an His tag to synthesize a soluble furin protease (furinΔC protease), followed by the Co column purification. Lane 2 shows only a recombinant activin A precursor protein including a Co column-purified zebrafish-derived prodomain. Lane 3 shows the reducing conditions for a mixture of the Co column-purified furinΔC protease and the recombinant activin A precursor protein including the zebrafish-derived prodomain. Lane 4 shows the non-reducing conditions for the mixture of the Co column-purified furinΔC protease and the recombinant activin A precursor protein including the zebrafish-derived prodomain. The furinΔC protease was obtained, using a plant cell, by synthesizing a soluble furin protease formed by deleting a lipid-raft region present at the C-terminus of a furin protease to convert the furin protease into the secreted soluble type while adding an His tag, as described in Bravo et al. ("Accurate and efficient cleavage of the human insulin proreceptor by the human proprotein-processing protease furin. Characterization and kinetic parameters using the purified, secreted soluble protease expressed by a recombinant baculovirus." J. Biol. Chem. 269, 25830-25837 (1994)) Although the Bravo et al. uses an insect cell, the synthesis can be made in the same manner using a plant cell. The furinΔC protease was synthesized and purified separately from the recombinant activin A precursor protein including the zebrafish-derived prodomain. In this way, the possibility that as a result of separation of a prodomain and a mature sequence, which is an active domain, due to the cleavage of the recombinant activin A precursor protein including the zebrafish-derived prodomain by the furin protease, the mature sequence was decomposed by an endogenous protease in the plant was avoided.

The furinΔC protease and the recombinant activin A precursor protein including the zebrafish-derived prodomain, which were purified separately, were mixed in a concentration ratio of 7:5 and treated at 30° C. for 30 minutes. As a result, most of the prodomains were cleaved and a band, which was considered to be active under the reducing conditions, was detected near the estimated molecular weight (about 12 kDa). In addition, under the non-reducing conditions, a thin band was detected near the estimated molecular weight (about 24 kDa) of a dimer, because of the poor recognition of the antibody, or other reasons.

8. Measurement of Bioactivity of Activin A

Since the band was detected near about 12 kDa, which was the estimated molecular weight of the active human activin A by cleaving the recombinant activin A precursor protein including the zebrafish-derived prodomain with the furinΔC protease, the bioactivity of the activin A based on the differentiation from the iPS cells to the definitive endoderm (DE) as an index was confirmed as follows.

Human iPS cells (1231A3 strain) maintained and cultured in an AK01 medium were sowed into a 96 well plate coated with iMatrix at 4×104 cells/well. After 24 hours, the medium was replaced with a DE differentiation medium (the activin A produced by the method as described herein or a commercial product, 2% B27 supplement, 3 μM CHIR99021) to initiate differentiation induction. The next day, the medium was replaced with a medium having the same composition and excluding CHIR99021, and thereafter, the medium was replaced every day. The evaluation was made using a commercial product of R&D systems as control, and the amount of Cerberus 1 in the culture supernatant was measured as an index of the DE differentiation. Note that Cerberus 1 is a secretory protein that expresses specifically to the DE stage, and activin A is known to be essential for the differentiation from iPS cells to DE.

Activin A produced by the method as described herein was evaluated using a partially purified mixed solution obtained by mixing furinΔC purified through the Co column and the recombinant activin A precursor protein including the zebrafish-derived prodomain. Since the recombinant activin A precursor protein synthesized in a plant by the method as described herein and purified through the Co column was in a partially purified state and the concentration was unclear, the partially purified mixed solution was added each in an amount of 1/1000 or 1/100 of the medium and used. The supernatant was recovered at the 5th day after the differentiation induction, and the amount of Cerberus 1 in the culture supernatant was quantified by the ELISA method using ES/iPS Differentiation Monitoring Kit (Dojindo, #ES01).

Figure 3:
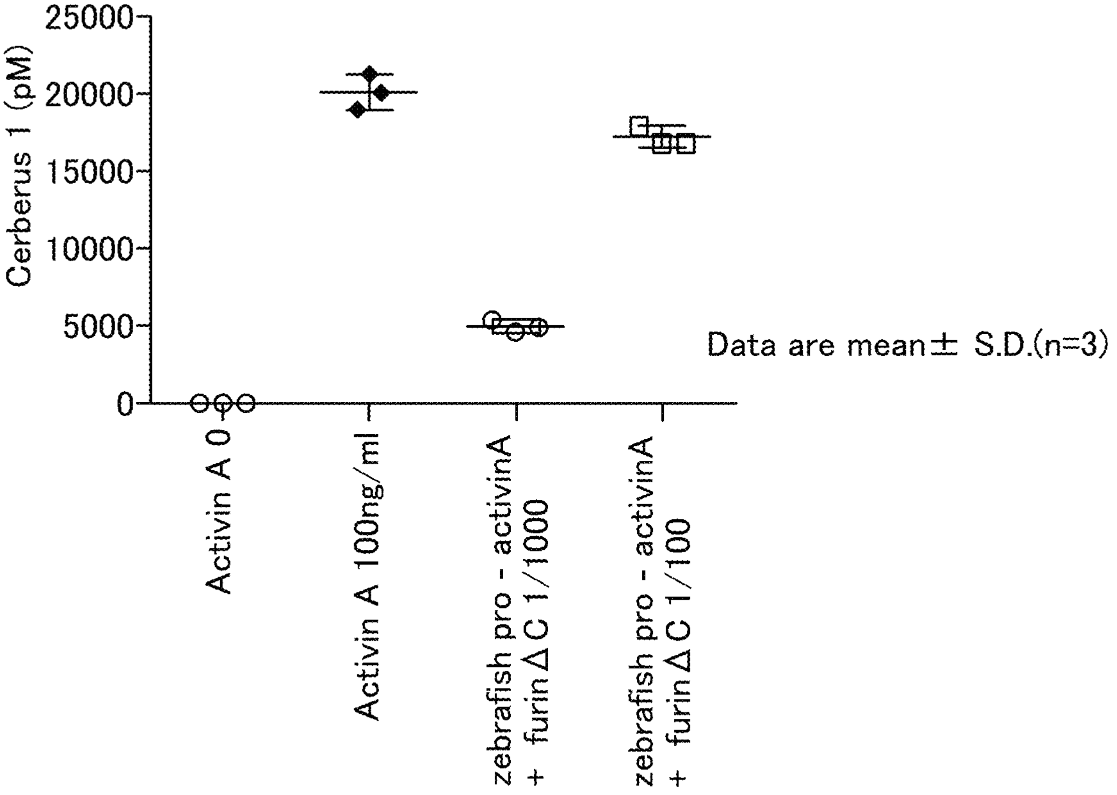
FIG. 3 illustrates a graph showing results of measuring the activin A bioactivity. The horizontal axis indicates, in order from the left, an experimental plot not containing activin A as a negative control (activin A 0); an experimental plot containing activin A produced by R&D systems as a positive control (activin A 100 ng/ml); an experimental plot containing activin A produced by the method as described herein in an amount of 1/1000 of the medium (the recombinant activin A precursor protein including the zebrafish-derived prodomain+furinΔC protease 1/1000); and an experimental plot containing activin A produced by the method as described herein in an amount of 1/100 of the medium (the recombinant activin A precursor protein including the zebrafish-derived prodomain+furinΔC protease 1/100). The vertical axis indicates the amount of Cerberus 1 (pM).

The results of measuring the activin A bioactivity are shown in FIG. 3. The horizontal axis indicates, in order from the left, an experimental plot not containing activin A as a negative control (activin A 0); an experimental plot containing activin A produced by R&D systems as a positive control (activin A 100 ng/ml); an experimental plot containing activin A produced by the method as described herein in an amount of 1/1000 of the medium (the recombinant activin A precursor protein including the zebrafish-derived prodomain+furinΔC 1/1000); and an experimental plot containing activin A produced by the method as described herein in an amount of 1/100 of the medium (the recombinant activin A precursor protein including the zebrafish-derived prodomain+furinΔC 1/100). The vertical axis indicates the amount of Cerberus 1 (pM).

As shown in FIG. 3, in the activity evaluation using DE differentiation as the index, concentration-dependent activity was observed in the human activin A generated by furin protease cleavage, produced using a plant by the method as described herein. In addition, the intensity of the activity was approximately 85% of the R&D 100 ng/mL with the addition in an amount of 1/100.

9. Evaluation of Activity by Smad Reporter Assay

The intensity of the Smad signal activated by activin A was quantified using Cignal Smad reporter assay (QIAGEN) using the human activin A generated by the recombinant activin A precursor protein and the furin protease cleavage, produced by the method as described herein.

First, to 25 μL of the Opti-MEM medium, 0.6 μL of the Attractene reagent (QIAGEN) was added, followed by incubation at room temperature for 5 minutes. To the above-mentioned mixed solution, a mixed solution of 25 μL of the Opti-MEM medium and 1 μL of the Smad reporter vector (QIAGEN) was added, followed by incubation at room temperature for 20 minutes. This mixed solution was added to the Collagen I-coated 96-well plate (IWAKI), and HEK293E cells at 40,000 cell/well were sowed and incubated in a 5% $CO_2$ incubator at 37° C. overnight to conduct transfection of the Smad reporter vector.

After the transfection was completed, all the culture supernatant was removed.

An Opti-MEM medium (starving medium) containing 0.5% FBS, 1% NEAA, and penicillin-streptomycin was added in an amount of 75 μL, followed by culturing at 37° C. for 4 hours to starve the cells.

The human activin A or the recombinant activin A precursor protein produced by the method as described herein or a starving medium to which activin A produced by R&D systems was added such that the concentration is twice the final concentration of the control was added in an amount of 75 μL to cells, followed by culturing in a 5% $CO_2$ incubator at 37° C. overnight to stimulate the cells. The human activin A produced by the method as described herein was evaluated using a partially purified mixed solution obtained by mixing furinΔC purified through the Co column and the recombinant activin A precursor protein including the African clawed frog or green sea turtle-derived prodomain in the same manner as in the above-described 8, and was used while being diluted at rates described in FIG. 4. The recombinant activin A precursor proteins synthesized in the plant by the method as described herein were as generated as described above, the recombinant activin A precursor protein including the zebrafish-derived prodomains used the protein extracts purified through the Ni column, and the other recombinant activin A precursor proteins used the protein extracts purified through the Co column, and these were used while being diluted at rates as described in FIGS. 4 and 5. For the concentration of the recombinant activin A precursor protein in each extract, the concentration of the recombinant activin A precursor protein including the African clawed frog-derived prodomain was 362 ng/μL, the concentration of the recombinant activin A precursor protein including the green sea turtle-derived prodomain was 63 ng/μL, the concentration of the recombinant activin A precursor protein including the zebrafish-derived prodomain was 332 ng/μL, the concentration of the recombinant activin A precursor protein including the channel catfish-derived prodomain was 178 ng/μL, and the concentration of the recombinant activin A precursor protein including the coelacanth-derived prodomain was 114 ng/μL. The concentrations were obtained by the Bradford method after the protein purification.

The Dual-Luciferase Reporter Assay System (Promega) was used for the reporter assay. First, 100 μL of the medium supernatant was removed, 50 μL of the Glo reagent was added, and cells were dissolved at room temperature for 10 minutes. The activation of the Smad pathway was quantified by detecting the light emission of Firefly luciferase emitted from the cell solution using a plate reader. Subsequently, 50 μL of a Glo & Stop reagent solution was added, and the light emission of Renilla luciferase, which is an internal standard, was detected after 10 minutes to quantify the number of cells. In accordance with the Smad activity=(the light emission intensity of Firefly luciferase)/(the light emission intensity of Renilla luciferase), the Smad activity of each sample was quantified. The relative value of the Smad activity for the sample (Mock) to which no activin A was added was obtained as Relative Smad activity.

Figure 4:
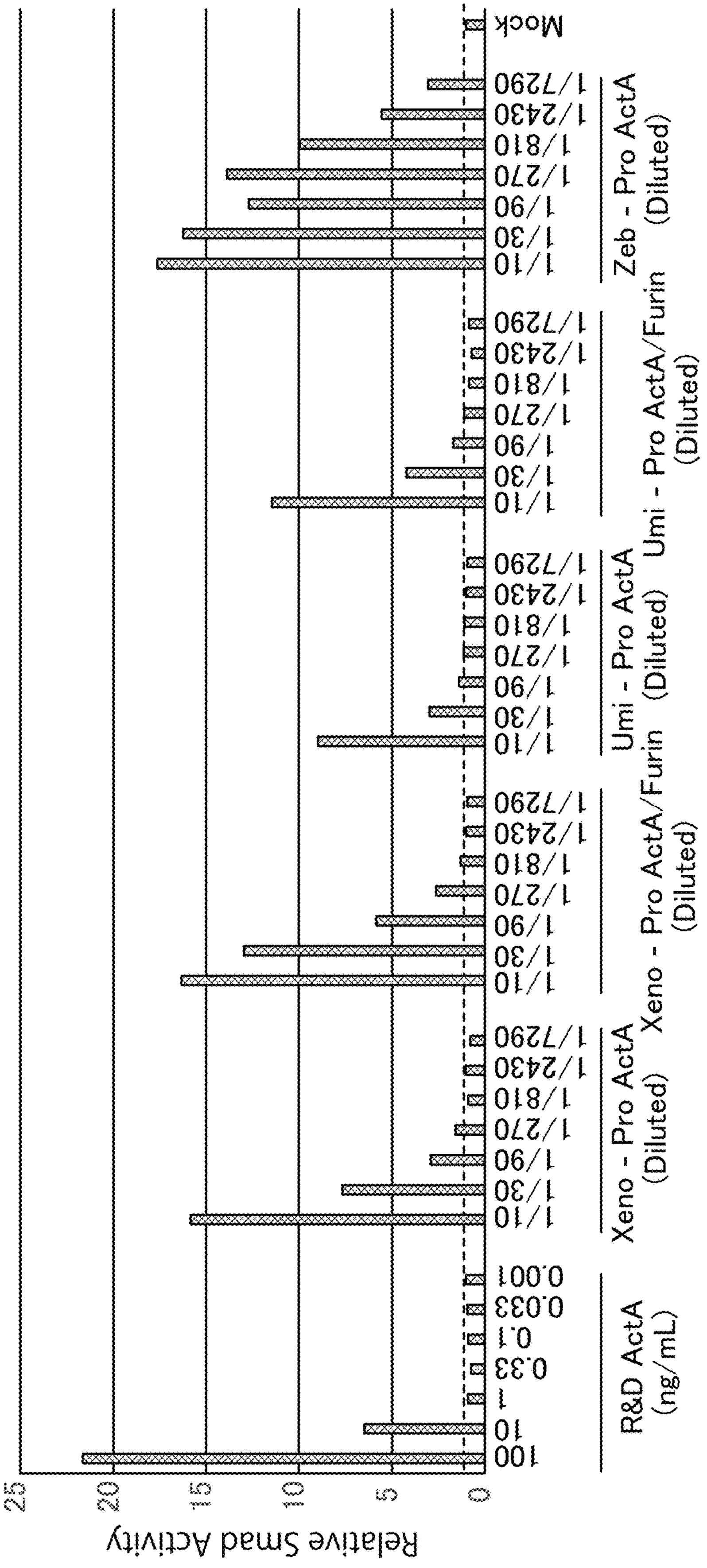
FIG. 4 illustrates a graph showing evaluation of activity of the recombinant activin A precursor protein by the Smad reporter assay.
Figure 5:
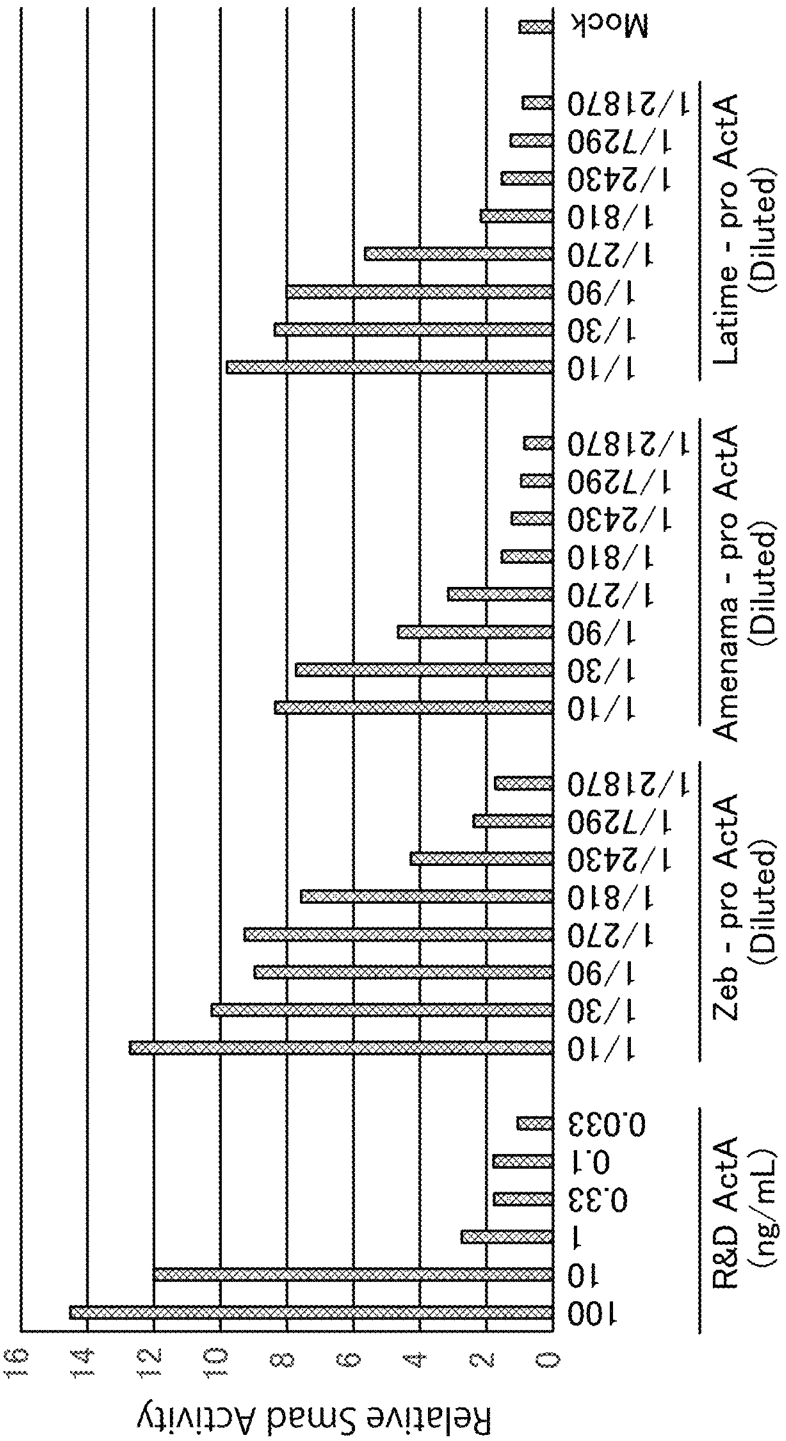
FIG. 5 illustrates a graph showing evaluation of activity of the recombinant activin A precursor protein by the Smad reporter assay.

The results are shown in FIGS. 4 and 5. FIG. 4 shows, in order from the left, the activin A produced by R&D systems, the recombinant activin A precursor protein including the African clawed frog-derived prodomain, the human activin A obtained by enzyme-cleaving the recombinant activin A precursor protein including the African clawed frog-derived prodomain, the recombinant activin A precursor protein including the green sea turtle-derived prodomain, the human activin A obtained by enzyme-cleaving the recombinant activin A precursor protein including the green sea turtle-derived prodomain, and the recombinant activin A precursor protein including the zebrafish-derived prodomain.

FIG. 5 shows, in order from the left, the activin A produced by R&D systems, the recombinant activin A precursor protein including the zebrafish-derived prodomain, the recombinant activin A precursor protein including the channel catfish-derived prodomain, and the recombinant activin A precursor protein including the coelacanth-derived prodomain.

From these results, it was revealed that all of the recombinant activin A precursor protein including the zebrafish-derived prodomain, the recombinant activin A precursor protein including the African clawed frog-derived prodomain, the recombinant activin A precursor protein including the green sea turtle-derived prodomain, the recombinant activin A precursor protein including the channel catfish-derived prodomain, and the recombinant activin A precursor protein including the coelacanth-derived prodomain had activity.

INDUSTRIAL APPLICABILITY

According to the present invention, it is possible to obtain an active protein without refolding even with a protein that is difficult to be folded such as activin. The method for producing human activin A is expected to be utilized for the industrial production of human activin A.

In addition, the recombinant activin A precursor protein of has human activin A activity unlike the conventional findings, and is therefore expected to be utilized in various fields.

What is claimed is:

1. A recombinant activin A precursor fusion protein comprising:

human mature activin A; and an activin A prodomain from amphibian, reptile, or fish;

wherein the recombinant activin A precursor fusion protein does not naturally occur.

2. The recombinant activin A precursor fusion protein according to claim 1, wherein the activin A prodomain is fish activin A prodomain.

3. The recombinant activin A precursor fusion protein according to claim 2, wherein the activin A prodomain comprises a sequence having 90% or more identity with the sequence shown in SEQ ID NO: 1.

4. The recombinant activin A precursor fusion protein according to claim 3, wherein the sequence having 90% or more identity with the sequence shown in SEQ ID NO: 1 is located at positions corresponding to positions 187 to 196 of the sequence shown in SEQ ID NO: 2.

5. The recombinant activin A precursor fusion protein according to claim 1, wherein the activin A prodomain has 90% or more identity with the sequence shown in SEQ ID NO: 2.

6. The recombinant activin A precursor fusion protein according to claim 1, wherein the activin A prodomain has 90% or more identity with the sequence shown in SEQ ID NO: 3.

7. The recombinant activin A precursor fusion protein according to claim 1, wherein the activin A prodomain has 90% or more identity with the sequence shown in SEQ ID NO: 4.

8. The recombinant activin A precursor fusion protein according to claim 1, wherein the activin A prodomain has 90% or more identity with the sequence shown in SEQ ID NO: 5.

9. The recombinant activin A precursor fusion protein according to claim 1, wherein the activin A prodomain has 90% or more identity with the sequence shown in SEQ ID NO: 6.

10. The recombinant activin A precursor fusion protein according to claim 1, wherein the recombinant activin A precursor fusion protein comprises a protease cleavable sequence between the human mature activin A and the activin A prodomain.

11. A polynucleotide encoding the recombinant activin A precursor fusion protein according to claim 1.

12. A recombinant vector comprising the polynucleotide according to claim 11.

13. A host cell comprising the polynucleotide encoding the recombinant activin A precursor fusion protein according to claim 11.

14. A method for producing the recombinant activin A precursor fusion protein according to claim 1, comprising:

introducing a polynucleotide encoding the recombinant activin A precursor fusion protein according to claim 1 into a plant cell or plant;

expressing the recombinant activin A precursor fusion protein according to claim 1 in the plant cell or plant, thereby producing the recombinant activin A precursor fusion protein.

15. A method for producing human activin A comprising the steps of:

introducing a polynucleotide encoding the recombinant activin A precursor fusion protein according to claim 10 into a plant cell or plant;

expressing the recombinant activin A precursor fusion protein according to claim 10 in the plant cell or plant; and treating the recombinant activin A precursor fusion protein with a protease, thereby producing the human activin A.

16. The method of claim 14, wherein the polynucleotide is present in a recombinant vector.

17. The method of claim 15, wherein the polynucleotide is present in a recombinant vector.

* * * * *

```
SEQUENCE LISTING

<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Common sequence

<400> SEQUENCE: 1

Asp Thr Arg Arg Ser Gly Trp His Thr Leu
1               5                   10


<210> SEQ ID NO 2
<211> LENGTH: 262
<212> TYPE: PRT
<213> ORGANISM: Danio rerio

<400> SEQUENCE: 2

Ser Pro Thr Pro Ser Asp Ser Gly Ser Pro Gly Ala Gly Arg Pro Asp
1               5                   10                  15
```

-continued

```
Asp Pro Val Thr Pro Cys Pro Ser Cys Ala Leu Ala Gln Arg Pro Lys
            20                  25                  30

Asp Ser Glu Glu Gln Ser Asp Met Val Glu Ala Val Lys Gln His Ile
        35                  40                  45

Leu Asn Met Leu His Leu Asn Thr Arg Pro Asn Val Thr His Pro Val
    50                  55                  60

Pro Arg Ala Ala Leu Leu Asn Ala Ile Arg Lys Pro His Val Gly Arg
65                  70                  75                  80

Val Gly Glu Asp Gly Thr Val Glu Met Glu Glu Asp Gly Gly Gly Leu
                85                  90                  95

Gly Glu His Arg Glu Gln Pro Glu Glu Gln Pro Phe Glu Ile Ile Thr
            100                 105                 110

Phe Ala Glu Pro Gly Asp Ala Pro Asp Val Leu Lys Phe Asp Ile Ser
        115                 120                 125

Lys Glu Gly Ser Thr Leu Ser Val Val Glu Gln Ala Asn Val Trp Leu
    130                 135                 140

Phe Leu Lys Val Ala Lys Gly Ser Arg Val Lys Gly Lys Val Ser Val
145                 150                 155                 160

Gln Leu Leu Gln Asn Gly Lys Ala Asp Ser Gly Ser Thr Asp Arg Pro
                165                 170                 175

Glu Asp Gln Val Val Ser Glu Lys Thr Ile Asp Thr Arg Arg Ser Gly
            180                 185                 190

Trp His Thr Leu Pro Val Pro Arg Thr Val Gln Thr Leu Leu Asp Gly
        195                 200                 205

Asp Ser Ser Leu Leu Ser Leu Arg Val Ser Cys Pro Met Cys Ala Glu
    210                 215                 220

Ala Gly Ala Val Pro Ile Leu Val Pro Ala Glu Gly Asn Lys Val Lys
225                 230                 235                 240

Glu Arg Glu Gln Ser His Arg Pro Phe Leu Met Val Val Leu Lys Pro
                245                 250                 255

Ala Glu Glu His Gln His
            260


<210> SEQ ID NO 3
<211> LENGTH: 270
<212> TYPE: PRT
<213> ORGANISM: Ictalurus punctatus

<400> SEQUENCE: 3

Ser Pro Thr Pro Ser Gly Met Gln Gly Thr Thr Pro Leu Glu Ser Glu
1               5                   10                  15

Arg Gln Glu Gly Ser Arg Gly Ala Glu Gln Gln Glu Glu Gly Gly Pro
            20                  25                  30

Val Ser Pro Cys Pro Ser Cys Ala Leu Ala Gln Leu Asp Arg Asp Ser
        35                  40                  45

Glu Pro Gly Met Val Glu Ala Val Lys Arg His Ile Leu Asn Met Leu
    50                  55                  60

His Leu Ser Ala Pro Pro Asn Ile Ser His Pro Val Pro Arg Ala Ala
65                  70                  75                  80

Leu Leu Asn Ala Leu Arg Lys Leu His Val Gly Arg Val Ala Gln Asp
                85                  90                  95

Gly Thr Val Glu Ile Glu Asp Glu Ala Glu Asp Phe Gly Gly His Ser
            100                 105                 110

Ala Gly Asp Glu Gln Pro Ser Glu Ile Ile Thr Phe Ala Glu Pro Val
        115                 120                 125
```

```
Asp Val Pro Asp Thr Val Lys Phe Asp Ile Ser Lys Glu Ser Ala Gly
    130                 135                 140

Gln Val Val Glu Gln Ala Asn Val Trp Ile Phe Leu Lys Leu Ala Lys
145                 150                 155                 160

Gly Ser His Ala Lys Gly Lys Val Ser Leu Gln Leu Leu Gln Ser Pro
                165                 170                 175

Ser Val Ser Thr Asp Ser Asn Pro Asp Pro Gln Asp Glu Val Leu Val
            180                 185                 190

Ser Gln Lys Met Val Asp Ala Arg Arg Ser Gly Trp His Thr Leu Ser
        195                 200                 205

Ile Gly Ala Ser Ala Gln Ala Leu Leu Asp Arg Gly Gly Gly Glu Leu
    210                 215                 220

Arg Phe Arg Val Ser Cys Pro Leu Cys Ala Asp Val Gly Ala Val Pro
225                 230                 235                 240

Ile Leu Gly Glu Gly Lys Gly Lys Glu His Ser Gln Ser His Arg Pro
                245                 250                 255

Phe Leu Met Leu Val Leu Arg Pro Ala Glu Asp Arg Gln His
            260                 265                 270


<210> SEQ ID NO 4
<211> LENGTH: 247
<212> TYPE: PRT
<213> ORGANISM: Latimeria chalumnae

<400> SEQUENCE: 4

Ser Pro Ala Leu Gly Val Glu Gly His Ser Ser Val Pro Glu Cys Ala
1               5                   10                  15

Ser Cys Ala Leu Ala Lys Leu Pro Lys Asp Thr Ser Ser Ser Pro Pro
            20                  25                  30

Ala Met Val Glu Ala Val Lys Lys His Ile Leu Asn Met Leu His Leu
        35                  40                  45

Lys Glu Arg Pro Asn Ile Thr Gln Ala Val Pro Arg Ala Ala Leu Leu
    50                  55                  60

Asn Ala Ile Lys Lys Leu His Val Gly Arg Val Gly Glu Asp Gly Asn
65                  70                  75                  80

Val Glu Ile Glu Asp Asp Ser Tyr Arg Arg Leu Glu Ala Thr Glu Met
                85                  90                  95

Ile Glu Gln Thr Ser Glu Ile Ile Thr Phe Ala Glu Ser Gly Ser Ser
            100                 105                 110

Gln Gly Leu Leu His Phe Gln Ile Ser Lys Glu Gly Asn Asp Leu Ser
        115                 120                 125

Val Val Glu Gln Ala Asn Ile Trp Leu Phe Leu Arg Leu Ser Lys Ser
    130                 135                 140

Asn Arg Ser Arg Ala Lys Val Thr Ile Arg Ile His Gln Lys His Arg
145                 150                 155                 160

Gly Ser Asn Gly Gln Asp Ile Glu Ser Val Ile Ser Glu Lys Ala Val
                165                 170                 175

Asp Thr Arg Arg Ser Gly Trp His Thr Leu Pro Val Ser Ser Ser Val
            180                 185                 190

Gln His Leu Leu Asp Gly Gly His Thr Ser Leu Asp Ile Arg Ile Ser
        195                 200                 205

Cys Ser Gln Cys Gln Glu Asn Gly Val Thr Pro Val Leu Val Glu Lys
    210                 215                 220

Glu Glu Lys Glu Gln Ser His Arg Pro Phe Leu Met Ile Leu Val Arg
```

225 230 235 240

Gln Ser Asp Asp His Pro His
245

<210> SEQ ID NO 5
<211> LENGTH: 231
<212> TYPE: PRT
<213> ORGANISM: Xenopus laevis

<400> SEQUENCE: 5

Ser Pro Thr Pro Glu Pro Gly Cys Pro Ser Cys His Pro Pro Met Glu
1 5 10 15

Pro Glu Met Leu Glu Ala Val Lys Arg His Ile Leu Thr Leu Leu His
20 25 30

Met Gln Asp Arg Pro Asn Ile Thr His Met Val Pro Arg Ala Ala Met
35 40 45

Val Ser Ala Leu Arg Lys Leu His Ala Gly Arg Val Arg Glu Asp Gly
50 55 60

Asn Leu Glu Ile Pro Asp Leu Asp Gly His Ser Leu Pro Pro Pro Gly
65 70 75 80

His Ser Thr Glu Asn Ser Ala Glu Ile Ile Thr Phe Ala Glu Thr Asp
85 90 95

Asp Val Thr Ala Ser Arg Val Arg Leu Ser Phe Thr Ile Ala Asn Glu
100 105 110

Gly Asn Gln Asn Leu Phe Val Phe Gln Ser Asn Leu Trp Leu Tyr Leu
115 120 125

Lys Leu Pro Glu Val Met Asp Lys Ser Arg Arg Lys Ile Arg Ile Lys
130 135 140

Val His Phe Gln Asp Ala Phe Asn Pro Asp Lys Met Asn Met Val Glu
145 150 155 160

Lys Lys Val Asp Ile Arg Arg Ser Gly Trp His Thr Phe Pro Leu Thr
165 170 175

Glu Ala Ile Gln Ser Leu Phe Glu Glu Gly Glu Arg Arg Leu Asn Leu
180 185 190

Glu Val Gln Cys Asp Gly Cys Gly Glu Tyr Ser Val Ile Pro Val Tyr
195 200 205

Val Asp Pro Gly Glu Glu Ser His Arg Pro Phe Leu Val Val His Ala
210 215 220

Arg Leu Ala Asp Asn Lys His
225 230

<210> SEQ ID NO 6
<211> LENGTH: 271
<212> TYPE: PRT
<213> ORGANISM: Chelonia mydas

<400> SEQUENCE: 6

His Ser Ser Val Thr Gly Cys Pro Ser Cys Ala Leu Ala Thr Leu Ser
1 5 10 15

Lys Asp Val Pro Ser Ser Gln Pro Glu Met Val Glu Ala Val Lys Lys
20 25 30

His Ile Leu Asn Met Leu His Leu Arg Asp Arg Pro Asn Ile Thr Gln
35 40 45

Pro Val Pro Lys Ala Ala Leu Leu Asn Ala Ile Lys Lys Leu His Val
50 55 60

Gly Lys Val Gly Glu Asp Gly Tyr Val Glu Ile Glu Asp Asp Ile Gly

-continued

```
65                  70                  75                  80

Arg Arg Ala Glu Met Asn Glu Leu Val Glu Gln Thr Ser Glu Ile Ile
                85                  90                  95

Thr Phe Ala Glu Ser Gly Thr Ala Lys Lys Met Leu His Phe Glu Ile
            100                 105                 110

Ser Lys Glu Gly Ser Asp Leu Ser Val Val Glu His Ala Glu Val Trp
        115                 120                 125

Leu Phe Leu Lys Val Ser Lys Ala Asn Arg Ser Arg Thr Lys Val Thr
    130                 135                 140

Ile Arg Leu Tyr Gln Gln Gln Arg Gln Pro Lys Gly Asn Ser Glu Gly
145                 150                 155                 160

Ala Glu Glu Met Glu Asp Gly Glu Leu Lys Gly Asp Lys Ser Glu Asn
                165                 170                 175

Leu Ile Ser Glu Lys Met Val Asp Thr Arg Lys Ser Thr Trp His Ile
            180                 185                 190

Phe Pro Val Ser Ser Ser Val Gln Tyr Leu Leu Asp Gln Gly Lys Ser
        195                 200                 205

Ser Leu Asp Val Arg Ile Ala Cys Asp Gln Cys Gln Glu Thr Gly Ala
    210                 215                 220

Ser Leu Val Leu Leu Gly Lys Lys Lys Lys Lys Glu Asp Lys Glu Lys
225                 230                 235                 240

Glu Val Gly Glu Ser Thr Val Glu Glu Glu Lys Glu Gln Ser His Arg
                245                 250                 255

Pro Phe Leu Met Met Leu Ala Arg His Ser Asp Asp Arg Leu His
            260                 265                 270


<210> SEQ ID NO 7
<211> LENGTH: 1260
<212> TYPE: DNA
<213> ORGANISM: Artificial Sequence
<220> FEATURE:
<223> OTHER INFORMATION: Recombinant DNA including Activin A prodomain
      of Danio rerio

<400> SEQUENCE: 7

atggctaaga ccaacctttt cctgttcctg atcttcagcc tgctgctgag cctttcttct     60

gctcatcatc accatcacca ctacccttac gatgtgcctg attacgcttc tcctacccct    120

agcgattctg gttctcctgg tgctggtaga cctgatgatc ctgttactcc ttgtccttct    180

tgcgctcttg ctcagaggcc taaggattct gaggaacaga gcgatatggt tgaggctgtg    240

aagcagcaca tcctgaacat gcttcacctt aacaccaggc ctaatgtgac tcatcctgtt    300

ccaagggctg ctctgcttaa cgctattagg aagcctcacg ttggtagggt tggagaggat    360

ggtactgttg agatggaaga ggatggtggt ggtcttggtg aacatagaga acagcctgaa    420

gaacagccat tcgagatcat cactttcgct gagcctggtg atgctcctga tgtgctgaag    480

ttcgatatca gcaaagaggg tagcaccctg tctgttgttg agcaggctaa tgtgtggctt    540

ttcctgaagg tggcaaaggg ttctagggtg aagggtaagg ttagcgtgca gcttcttcag    600

aacggtaagg ctgatagcgg ttctactgat aggcctgagg atcaggtggt gagcgaaaag    660

accattgata ccagaaggtc tggttggcac actttgccag ttcctaggac tgtgcagacc    720

cttctggatg gtgatagctc tctgctttct ctgagggtgt catgtcctat gtgtgctgag    780

gctggtgctg tgcctattct tgttcctgct gagggtaaca aggtgaaaga gagagagcag    840

tctcacaggc ctttcttgat ggtggttttg aagcctgcag aggaacacca gcacagaagg    900
```

```
tctaagcgtg gacttgaatg tgatggtaag gttaatattt gctgtaaaaa gcaatttttc    960

gtttctttta aagatattgg atggaatgat tggattattg ctccatctgg ttatcatgct   1020

aattattgtg aaggagagtg tccttctcat attgctggta cttctggatc ttcattgtca   1080

tttcattcta ctgttattaa tcattataga atgaggggtc attctccatt tgctaatctt   1140

aagtcttgtt gtgttccaac taagttgaga ccaatgtcta tgctttacta tgatgatgga   1200

caaaatatta ttaaaaagga tattcaaaat atgattgttg aagagtgtgg atgctcttag   1260
```

<210> SEQ ID NO 8
<211> LENGTH: 419
<212> TYPE: PRT
<213> ORGANISM: Artificial Sequence
<220> FEATURE:
<223> OTHER INFORMATION: Recombinant Protein including Activin A prodomain of Danio rerio

<400> SEQUENCE: 8

```
Met Ala Lys Thr Asn Leu Phe Leu Phe Leu Ile Phe Ser Leu Leu Leu
1               5                   10                  15

Ser Leu Ser Ser Ala His His His His His His Tyr Pro Tyr Asp Val
            20                  25                  30

Pro Asp Tyr Ala Ser Pro Thr Pro Ser Asp Ser Gly Ser Pro Gly Ala
        35                  40                  45

Gly Arg Pro Asp Asp Pro Val Thr Pro Cys Pro Ser Cys Ala Leu Ala
    50                  55                  60

Gln Arg Pro Lys Asp Ser Glu Glu Gln Ser Asp Met Val Glu Ala Val
65                  70                  75                  80

Lys Gln His Ile Leu Asn Met Leu His Leu Asn Thr Arg Pro Asn Val
                85                  90                  95

Thr His Pro Val Pro Arg Ala Ala Leu Leu Asn Ala Ile Arg Lys Pro
            100                 105                 110

His Val Gly Arg Val Gly Glu Asp Gly Thr Val Glu Met Glu Glu Asp
        115                 120                 125

Gly Gly Gly Leu Gly Glu His Arg Glu Gln Pro Glu Glu Gln Pro Phe
    130                 135                 140

Glu Ile Ile Thr Phe Ala Glu Pro Gly Asp Ala Pro Asp Val Leu Lys
145                 150                 155                 160

Phe Asp Ile Ser Lys Glu Gly Ser Thr Leu Ser Val Val Glu Gln Ala
                165                 170                 175

Asn Val Trp Leu Phe Leu Lys Val Ala Lys Gly Ser Arg Val Lys Gly
            180                 185                 190

Lys Val Ser Val Gln Leu Leu Gln Asn Gly Lys Ala Asp Ser Gly Ser
        195                 200                 205

Thr Asp Arg Pro Glu Asp Gln Val Val Ser Glu Lys Thr Ile Asp Thr
    210                 215                 220

Arg Arg Ser Gly Trp His Thr Leu Pro Val Pro Arg Thr Val Gln Thr
225                 230                 235                 240

Leu Leu Asp Gly Asp Ser Ser Leu Leu Ser Leu Arg Val Ser Cys Pro
                245                 250                 255

Met Cys Ala Glu Ala Gly Ala Val Pro Ile Leu Val Pro Ala Glu Gly
            260                 265                 270

Asn Lys Val Lys Glu Arg Glu Gln Ser His Arg Pro Phe Leu Met Val
        275                 280                 285

Val Leu Lys Pro Ala Glu Glu His Gln His Arg Arg Ser Lys Arg Gly
    290                 295                 300
```

```
Leu Glu Cys Asp Gly Lys Val Asn Ile Cys Cys Lys Lys Gln Phe Phe
305                 310                 315                 320

Val Ser Phe Lys Asp Ile Gly Trp Asn Asp Trp Ile Ile Ala Pro Ser
                325                 330                 335

Gly Tyr His Ala Asn Tyr Cys Glu Gly Glu Cys Pro Ser His Ile Ala
            340                 345                 350

Gly Thr Ser Gly Ser Ser Leu Ser Phe His Ser Thr Val Ile Asn His
        355                 360                 365

Tyr Arg Met Arg Gly His Ser Pro Phe Ala Asn Leu Lys Ser Cys Cys
    370                 375                 380

Val Pro Thr Lys Leu Arg Pro Met Ser Met Leu Tyr Tyr Asp Asp Gly
385                 390                 395                 400

Gln Asn Ile Ile Lys Lys Asp Ile Gln Asn Met Ile Val Glu Glu Cys
                405                 410                 415

Gly Cys Ser
```

<210> SEQ ID NO 9
<211> LENGTH: 1284
<212> TYPE: DNA
<213> ORGANISM: Artificial Sequence
<220> FEATURE:
<223> OTHER INFORMATION: Recombinant DNA including Activin A prodomain of Ictalurus punctatus

<400> SEQUENCE: 9

```
atggctaaga ctaacctttt cctgttcctg atcttcagcc tgctgctgag cctttcttct     60

gctcatcatc accatcacca ctacccttac gatgtgcctg attacgcttc tccaactcca    120

tctggtatgc agggtactac ccctcttgag tctgaaaggc aagagggttc tagaggtgct    180

gagcaacaag aggaaggtgg tcctgtttct ccttgtcctt cttgtgctct tgctcagctg    240

gatagggatt ctgagcctgg tatggttgag gctgtgaaga ggcacattct gaacatgctt    300

cacctgagcg ctcctccgaa tatttctcat cctgttccaa gggctgctct gctgaacgct    360

cttagaaagc ttcatgtggg tagagtggct caggatggca ctgttgaaat tgaggatgag    420

gctgaggatt tcggtggtca ctctgctggt gatgaacagc cttctgagat catcactttc    480

gctgagcctg tggatgtgcc tgataccgtg aagttcgaca tcagcaaaga gagcgctggc    540

caagttgttg agcaggctaa tgtgtggatc ttcctgaagc tggctaaggg ctctcacgct    600

aagggtaaag tgtctcttca gctcctgcag tccccttctg tgtctactga ttctaaccct    660

gatccgcagg atgaggtgct ggtgtctcaa aagatggtgg atgctagaag gtctggttgg    720

cacacccttt ctattggtgc ttcagctcag gctctgcttg atagaggtgg tggtgagctt    780

aggttcagag tgtcttgtcc tctttgcgct gatgttggtg ctgtgcctat tcttggtgaa    840

ggcaagggaa aagagcacag ccagtctcat aggccgttcc ttatgcttgt tcttaggcct    900

gctgaggaca ggcaacatag aaggtctaag cgtggacttg aatgtgatgg taaggttaat    960

atttgctgta aaaagcaatt tttcgtttct tttaaagata ttggatggaa tgattggatt   1020

attgctccat ctggttatca tgctaattat tgtgaaggag agtgtccttc tcatattgct   1080

ggtacttctg gatcttcatt gtcatttcat tctactgtta ttaatcatta tagaatgagg   1140

ggtcattctc catttgctaa tcttaagtct tgttgtgttc caactaagtt gagaccaatg   1200

tctatgcttt actatgatga tggacaaaat attattaaaa aggatattca aaatatgatt   1260

gttgaagagt gtggatgctc ttag                                          1284
```

<210> SEQ ID NO 10
<211> LENGTH: 427
<212> TYPE: PRT
<213> ORGANISM: Artificial Sequence
<220> FEATURE:
<223> OTHER INFORMATION: Recombinant Protein including Activin A prodomain of Ictalurus punctatus

<400> SEQUENCE: 10

```
Met Ala Lys Thr Asn Leu Phe Leu Phe Leu Ile Phe Ser Leu Leu Leu
1               5                   10                  15

Ser Leu Ser Ser Ala His His His His His His Tyr Pro Tyr Asp Val
            20                  25                  30

Pro Asp Tyr Ala Ser Pro Thr Pro Ser Gly Met Gln Gly Thr Thr Pro
        35                  40                  45

Leu Glu Ser Glu Arg Gln Glu Gly Ser Arg Gly Ala Glu Gln Gln Glu
    50                  55                  60

Glu Gly Gly Pro Val Ser Pro Cys Pro Ser Cys Ala Leu Ala Gln Leu
65                  70                  75                  80

Asp Arg Asp Ser Glu Pro Gly Met Val Glu Ala Val Lys Arg His Ile
                85                  90                  95

Leu Asn Met Leu His Leu Ser Ala Pro Pro Asn Ile Ser His Pro Val
            100                 105                 110

Pro Arg Ala Ala Leu Leu Asn Ala Leu Arg Lys Leu His Val Gly Arg
        115                 120                 125

Val Ala Gln Asp Gly Thr Val Glu Ile Glu Asp Glu Ala Glu Asp Phe
    130                 135                 140

Gly Gly His Ser Ala Gly Asp Glu Gln Pro Ser Glu Ile Ile Thr Phe
145                 150                 155                 160

Ala Glu Pro Val Asp Val Pro Asp Thr Val Lys Phe Asp Ile Ser Lys
                165                 170                 175

Glu Ser Ala Gly Gln Val Val Glu Gln Ala Asn Val Trp Ile Phe Leu
            180                 185                 190

Lys Leu Ala Lys Gly Ser His Ala Lys Gly Lys Val Ser Leu Gln Leu
        195                 200                 205

Leu Gln Ser Pro Ser Val Ser Thr Asp Ser Asn Pro Asp Pro Gln Asp
    210                 215                 220

Glu Val Leu Val Ser Gln Lys Met Val Asp Ala Arg Arg Ser Gly Trp
225                 230                 235                 240

His Thr Leu Ser Ile Gly Ala Ser Ala Gln Ala Leu Leu Asp Arg Gly
                245                 250                 255

Gly Gly Glu Leu Arg Phe Arg Val Ser Cys Pro Leu Cys Ala Asp Val
            260                 265                 270

Gly Ala Val Pro Ile Leu Gly Glu Gly Lys Gly Lys Glu His Ser Gln
        275                 280                 285

Ser His Arg Pro Phe Leu Met Leu Val Leu Arg Pro Ala Glu Asp Arg
    290                 295                 300

Gln His Arg Arg Ser Lys Arg Gly Leu Glu Cys Asp Gly Lys Val Asn
305                 310                 315                 320

Ile Cys Cys Lys Lys Gln Phe Phe Val Ser Phe Lys Asp Ile Gly Trp
                325                 330                 335

Asn Asp Trp Ile Ile Ala Pro Ser Gly Tyr His Ala Asn Tyr Cys Glu
            340                 345                 350

Gly Glu Cys Pro Ser His Ile Ala Gly Thr Ser Gly Ser Ser Leu Ser
        355                 360                 365
```

```
Phe His Ser Thr Val Ile Asn His Tyr Arg Met Arg Gly His Ser Pro
    370                 375                 380

Phe Ala Asn Leu Lys Ser Cys Cys Val Pro Thr Lys Leu Arg Pro Met
385                 390                 395                 400

Ser Met Leu Tyr Tyr Asp Asp Gly Gln Asn Ile Ile Lys Lys Asp Ile
                405                 410                 415

Gln Asn Met Ile Val Glu Glu Cys Gly Cys Ser
            420                 425
```

<210> SEQ ID NO 11
<211> LENGTH: 1215
<212> TYPE: DNA
<213> ORGANISM: Artificial Sequence
<220> FEATURE:
<223> OTHER INFORMATION: Recombinant DNA including Activin A prodomain of Latimeria chalumnae

<400> SEQUENCE: 11

```
atggctaaga ctaacctttt cctgttcctg atcttcagcc tgctgctgag cctttcttct     60

gctcatcatc accaccatca ctacccttac gatgtgcctg attacgcttc tcctgctctt    120

ggtgttgagg gacattcttc tgttccagag tgtgcttctt gcgctcttgc taagcttccg    180

aaggatacct cttctagccc tcctgctatg gttgaggctg tgaagaaaca catcctgaac    240

atgctgcacc tgaaagagag gcctaacatt actcaggctg ttcctagggc tgctctgctg    300

aacgctatta agaagctgca cgttggtaga gttggcgagg atggtaacgt tgagatcgag    360

gatgatagct acaggcggct tgaagctacc gagatgattg aacagaccag cgagatcatc    420

accttcgctg agtctggttc ttctcagggt ttgctgcact tccagatcag caaagagggc    480

aacgatctgt ctgttgtcga gcaggctaac atctggcttt ttctgcggct gagcaagagc    540

aacaggtcta gagctaaggt gaccatccgg attcaccaaa agcacagggg ttctaacggt    600

caggatatcg agtctgtgat cagcgagaag gctgtggata caagaaggtc tggttggcac    660

actctcccgg tttcttctag tgtgcagcac cttcttgatg gtggccacac ctctcttgac    720

atcaggattt cttgcagcca gtgccaagag aatggtgtga ctcctgtgct ggtcgagaaa    780

gaagagaaag agcagtctca ccggccgttc cttatgattc ttgtgaggca gtctgacgat    840

caccctcaca gacgtaagaa acggggactt gaatgtgatg gtaaggttaa tatttgctgt    900

aaaaagcaat ttttcgtttc ttttaaagat attggatgga atgattggat tattgctcca    960

tctggttatc atgctaatta ttgtgaagga gagtgtcctt ctcatattgc tggtacttct   1020

ggatcttcat tgtcatttca ttctactgtt attaatcatt atagaatgag gggtcattct   1080

ccatttgcta atcttaagtc ttgttgtgtt ccaactaagt tgagaccaat gtctatgctt   1140

tactatgatg atggacaaaa tattattaaa aaggatattc aaaatatgat tgttgaagag   1200

tgtggatgct cttag                                                    1215
```

<210> SEQ ID NO 12
<211> LENGTH: 404
<212> TYPE: PRT
<213> ORGANISM: Artificial Sequence
<220> FEATURE:
<223> OTHER INFORMATION: Recombinant Protein including Activin A prodomain of Latimeria chalumnae

<400> SEQUENCE: 12

```
Met Ala Lys Thr Asn Leu Phe Leu Phe Leu Ile Phe Ser Leu Leu Leu
1               5                   10                  15
```

-continued

```
Ser Leu Ser Ser Ala His His His His His His Tyr Pro Tyr Asp Val
            20                  25                  30

Pro Asp Tyr Ala Ser Pro Ala Leu Gly Val Glu Gly His Ser Ser Val
        35                  40                  45

Pro Glu Cys Ala Ser Cys Ala Leu Ala Lys Leu Pro Lys Asp Thr Ser
    50                  55                  60

Ser Ser Pro Pro Ala Met Val Glu Ala Val Lys Lys His Ile Leu Asn
65                  70                  75                  80

Met Leu His Leu Lys Glu Arg Pro Asn Ile Thr Gln Ala Val Pro Arg
                85                  90                  95

Ala Ala Leu Leu Asn Ala Ile Lys Lys Leu His Val Gly Arg Val Gly
            100                 105                 110

Glu Asp Gly Asn Val Glu Ile Glu Asp Asp Ser Tyr Arg Arg Leu Glu
        115                 120                 125

Ala Thr Glu Met Ile Glu Gln Thr Ser Glu Ile Ile Thr Phe Ala Glu
    130                 135                 140

Ser Gly Ser Ser Gln Gly Leu Leu His Phe Gln Ile Ser Lys Glu Gly
145                 150                 155                 160

Asn Asp Leu Ser Val Val Glu Gln Ala Asn Ile Trp Leu Phe Leu Arg
                165                 170                 175

Leu Ser Lys Ser Asn Arg Ser Arg Ala Lys Val Thr Ile Arg Ile His
            180                 185                 190

Gln Lys His Arg Gly Ser Asn Gly Gln Asp Ile Glu Ser Val Ile Ser
        195                 200                 205

Glu Lys Ala Val Asp Thr Arg Arg Ser Gly Trp His Thr Leu Pro Val
    210                 215                 220

Ser Ser Ser Val Gln His Leu Leu Asp Gly Gly His Thr Ser Leu Asp
225                 230                 235                 240

Ile Arg Ile Ser Cys Ser Gln Cys Gln Glu Asn Gly Val Thr Pro Val
                245                 250                 255

Leu Val Glu Lys Glu Glu Lys Glu Gln Ser His Arg Pro Phe Leu Met
            260                 265                 270

Ile Leu Val Arg Gln Ser Asp Asp His Pro His Arg Arg Lys Lys Arg
        275                 280                 285

Gly Leu Glu Cys Asp Gly Lys Val Asn Ile Cys Cys Lys Lys Gln Phe
    290                 295                 300

Phe Val Ser Phe Lys Asp Ile Gly Trp Asn Asp Trp Ile Ile Ala Pro
305                 310                 315                 320

Ser Gly Tyr His Ala Asn Tyr Cys Glu Gly Glu Cys Pro Ser His Ile
                325                 330                 335

Ala Gly Thr Ser Gly Ser Ser Leu Ser Phe His Ser Thr Val Ile Asn
            340                 345                 350

His Tyr Arg Met Arg Gly His Ser Pro Phe Ala Asn Leu Lys Ser Cys
        355                 360                 365

Cys Val Pro Thr Lys Leu Arg Pro Met Ser Met Leu Tyr Tyr Asp Asp
    370                 375                 380

Gly Gln Asn Ile Ile Lys Lys Asp Ile Gln Asn Met Ile Val Glu Glu
385                 390                 395                 400

Cys Gly Cys Ser
```

<210> SEQ ID NO 13
<211> LENGTH: 1167
<212> TYPE: DNA

-continued

<213> ORGANISM: Artificial Sequence
<220> FEATURE:
<223> OTHER INFORMATION: Recombinant DNA including Activin A prodomain of Xenopus laevis

<400> SEQUENCE: 13

```
atggctaaga ccaacctttt cctgttcctg atcttcagcc tgctgctgag cctttcttct      60

gctcatcatc accatcacca ctacccttac gatgtgcctg attacgcttc tcctactcct     120

gaacctggtt gcccttcttg tcatcctcct atggaacctg agatgcttga ggctgtgaag     180

aggcacattc ttaccctgct tcacatgcag gataggccta acattaccca catggttcct     240

agggctgcta tggtgtctgc tcttagaaag cttcatgctg gtagggtgag agaggatggt     300

aaccttgaga tccctgatct ggatggtcac tctttgcctc cacctggtca ttctactgag     360

aacagcgctg agatcatcac cttcgctgag actgatgatg tgaccgcttc tagggtgagg     420

ctgtctttca ctattgctaa cgagggtaac cagaacctgt tcgtgttcca gtctaacctg     480

tggctgtacc ttaagctgcc tgaggtgatg gataagtcta gaagaaagat taggatcaag     540

gtgcacttcc aggatgcttt caaccctgat aagatgaaca tggttgagaa gaaagtggat     600

atcagaaggt ccggttggca cacctttcca cttactgagg ctatccagtc cctgttcgaa     660

gaaggtgaga gaaggcttaa cttggaggtg cagtgtgatg gttgcggtga gtactctgtg     720

atccctgtgt atgttgatcc tggtgaagag agccacaggc ctttcttggt tgttcatgct     780

aggctggctg ataacaagca ccggatccgt aagaggggac ttgaatgtga tggtaaggtt     840

aatatttgct gtaaaaagca atttttcgtt tcttttaaag atattggatg gaatgattgg     900

attattgctc catctggtta tcatgctaat tattgtgaag gagagtgtcc ttctcatatt     960

gctggtactt ctggatcttc attgtcattt cattctactg ttattaatca ttatagaatg    1020

aggggtcatt ctccatttgc taatcttaag tcttgttgtg ttccaactaa gttgagacca    1080

atgtctatgc tttactatga tgatggacaa aatattatta aaaaggatat tcaaaatatg    1140

attgttgaag agtgtggatg ctcttaa                                        1167
```

<210> SEQ ID NO 14
<211> LENGTH: 388
<212> TYPE: PRT
<213> ORGANISM: Artificial Sequence
<220> FEATURE:
<223> OTHER INFORMATION: Recombinant Protein including Activin A prodomain of Xenopus laevis

<400> SEQUENCE: 14

```
Met Ala Lys Thr Asn Leu Phe Leu Phe Leu Ile Phe Ser Leu Leu Leu
1               5                   10                  15

Ser Leu Ser Ser Ala His His His His His His Tyr Pro Tyr Asp Val
            20                  25                  30

Pro Asp Tyr Ala Ser Pro Thr Pro Glu Pro Gly Cys Pro Ser Cys His
        35                  40                  45

Pro Pro Met Glu Pro Glu Met Leu Glu Ala Val Lys Arg His Ile Leu
    50                  55                  60

Thr Leu Leu His Met Gln Asp Arg Pro Asn Ile Thr His Met Val Pro
65                  70                  75                  80

Arg Ala Ala Met Val Ser Ala Leu Arg Lys Leu His Ala Gly Arg Val
                85                  90                  95

Arg Glu Asp Gly Asn Leu Glu Ile Pro Asp Leu Asp Gly His Ser Leu
            100                 105                 110
```

-continued

```
Pro Pro Pro Gly His Ser Thr Glu Asn Ser Ala Glu Ile Ile Thr Phe
        115                 120                 125

Ala Glu Thr Asp Asp Val Thr Ala Ser Arg Val Arg Leu Ser Phe Thr
    130                 135                 140

Ile Ala Asn Glu Gly Asn Gln Asn Leu Phe Val Phe Gln Ser Asn Leu
145                 150                 155                 160

Trp Leu Tyr Leu Lys Leu Pro Glu Val Met Asp Lys Ser Arg Arg Lys
                165                 170                 175

Ile Arg Ile Lys Val His Phe Gln Asp Ala Phe Asn Pro Asp Lys Met
            180                 185                 190

Asn Met Val Glu Lys Lys Val Asp Ile Arg Arg Ser Gly Trp His Thr
        195                 200                 205

Phe Pro Leu Thr Glu Ala Ile Gln Ser Leu Phe Glu Glu Gly Glu Arg
    210                 215                 220

Arg Leu Asn Leu Glu Val Gln Cys Asp Gly Cys Gly Glu Tyr Ser Val
225                 230                 235                 240

Ile Pro Val Tyr Val Asp Pro Gly Glu Glu Ser His Arg Pro Phe Leu
                245                 250                 255

Val Val His Ala Arg Leu Ala Asp Asn Lys His Arg Ile Arg Lys Arg
            260                 265                 270

Gly Leu Glu Cys Asp Gly Lys Val Asn Ile Cys Cys Lys Lys Gln Phe
        275                 280                 285

Phe Val Ser Phe Lys Asp Ile Gly Trp Asn Asp Trp Ile Ile Ala Pro
    290                 295                 300

Ser Gly Tyr His Ala Asn Tyr Cys Glu Gly Glu Cys Pro Ser His Ile
305                 310                 315                 320

Ala Gly Thr Ser Gly Ser Ser Leu Ser Phe His Ser Thr Val Ile Asn
                325                 330                 335

His Tyr Arg Met Arg Gly His Ser Pro Phe Ala Asn Leu Lys Ser Cys
            340                 345                 350

Cys Val Pro Thr Lys Leu Arg Pro Met Ser Met Leu Tyr Tyr Asp Asp
        355                 360                 365

Gly Gln Asn Ile Ile Lys Lys Asp Ile Gln Asn Met Ile Val Glu Glu
    370                 375                 380

Cys Gly Cys Ser
385

<210> SEQ ID NO 15
<211> LENGTH: 1260
<212> TYPE: DNA
<213> ORGANISM: Artificial Sequence
<220> FEATURE:
<223> OTHER INFORMATION: Recombinant DNA including Activin A prodomain
      of Chelonia mydas

<400> SEQUENCE: 15
atggctaaga ccaacctttt cctgttcctg atcttcagcc tgctgctgag cctttcttct     60
gctcatcatc accatcacca tcattcttct gtgaccggtt gcccttcttg tgctcttgct    120
accctttcta aggatgtgcc atctagccag cctgagatgg ttgaggctgt gaagaaacac    180
atcctgaaca tgctgcacct gagggatagg cctaatatta ctcagcctgt gcctaaggct    240
gctctgctga acgctattaa gaagctgcac gttggtaagg tgggagagga tggttacgtt    300
gagatcgagg atgatatcgg tagaagggct gagatgaacg agcttgttga gcagacctct    360
gagatcatca ccttcgctga atctggaacc gctaagaaga tgctgcactt cgagatcagc    420
```

```
aaagagggta gcgatctgtc tgtggttgag catgctgagg tgtggctttt cctgaaggtg    480

tcaaaggcta acaggtccag gaccaaggtg accattaggc tttatcaaca acagaggcag    540

cctaagggaa actctgaagg tgctgaagag atggaagatg gtgagctgaa gggtgataag    600

agcgagaacc tgatcagcga aaagatggtg gataccagaa agagcacctg gcacatcttc    660

cctgtgtcat cttctgtgca gtacctgctg gatcagggta agagttctct ggatgtgagg    720

atcgcttgcg atcagtgtca agagactggt gcttctcttg tgctgctggg taagaagaag    780

aaaaaagagg ataaagagaa agaggttgga gagtccaccg ttgaggaaga aaaagagcag    840

tctcacaggc ctttcttgat gatgcttgct aggcactccg atgataggct tcaccgtaga    900

cgtagacgtg gacttgaatg tgatggtaag gttaatattt gctgtaaaaa gcaatttttc    960

gtttctttta aagatattgg atggaatgat tggattattg ctccatctgg ttatcatgct   1020

aattattgtg aaggagagtg tccttctcat attgctggta cttctggatc ttcattgtca   1080

tttcattcta ctgttattaa tcattataga atgaggggtc attctccatt tgctaatctt   1140

aagtcttgtt gtgttccaac taagttgaga ccaatgtcta tgctttacta tgatgatgga   1200

caaaatatta ttaaaaagga tattcaaaat atgattgttg aagagtgtgg atgctcttag   1260
```

<210> SEQ ID NO 16
<211> LENGTH: 419
<212> TYPE: PRT
<213> ORGANISM: Artificial Sequence
<220> FEATURE:
<223> OTHER INFORMATION: Recombinant Protein including Activin A prodomain of Chelonia mydas

<400> SEQUENCE: 16

```
Met Ala Lys Thr Asn Leu Phe Leu Phe Leu Ile Phe Ser Leu Leu Leu
1               5                   10                  15

Ser Leu Ser Ser Ala His His His His His His His Ser Ser Val Thr
            20                  25                  30

Gly Cys Pro Ser Cys Ala Leu Ala Thr Leu Ser Lys Asp Val Pro Ser
        35                  40                  45

Ser Gln Pro Glu Met Val Glu Ala Val Lys Lys His Ile Leu Asn Met
    50                  55                  60

Leu His Leu Arg Asp Arg Pro Asn Ile Thr Gln Pro Val Pro Lys Ala
65                  70                  75                  80

Ala Leu Leu Asn Ala Ile Lys Lys Leu His Val Gly Lys Val Gly Glu
                85                  90                  95

Asp Gly Tyr Val Glu Ile Glu Asp Asp Ile Gly Arg Arg Ala Glu Met
            100                 105                 110

Asn Glu Leu Val Glu Gln Thr Ser Glu Ile Ile Thr Phe Ala Glu Ser
        115                 120                 125

Gly Thr Ala Lys Lys Met Leu His Phe Glu Ile Ser Lys Glu Gly Ser
    130                 135                 140

Asp Leu Ser Val Val Glu His Ala Glu Val Trp Leu Phe Leu Lys Val
145                 150                 155                 160

Ser Lys Ala Asn Arg Ser Arg Thr Lys Val Thr Ile Arg Leu Tyr Gln
                165                 170                 175

Gln Gln Arg Gln Pro Lys Gly Asn Ser Glu Gly Ala Glu Glu Met Glu
            180                 185                 190

Asp Gly Glu Leu Lys Gly Asp Lys Ser Glu Asn Leu Ile Ser Glu Lys
        195                 200                 205

Met Val Asp Thr Arg Lys Ser Thr Trp His Ile Phe Pro Val Ser Ser
```

-continued

```
    210                 215                 220

Ser Val Gln Tyr Leu Leu Asp Gln Gly Lys Ser Ser Leu Asp Val Arg
225                 230                 235                 240

Ile Ala Cys Asp Gln Cys Gln Glu Thr Gly Ala Ser Leu Val Leu Leu
                245                 250                 255

Gly Lys Lys Lys Lys Lys Glu Asp Lys Glu Lys Glu Val Gly Glu Ser
            260                 265                 270

Thr Val Glu Glu Glu Lys Glu Gln Ser His Arg Pro Phe Leu Met Met
        275                 280                 285

Leu Ala Arg His Ser Asp Asp Arg Leu His Arg Arg Arg Arg Arg Gly
    290                 295                 300

Leu Glu Cys Asp Gly Lys Val Asn Ile Cys Cys Lys Lys Gln Phe Phe
305                 310                 315                 320

Val Ser Phe Lys Asp Ile Gly Trp Asn Asp Trp Ile Ile Ala Pro Ser
                325                 330                 335

Gly Tyr His Ala Asn Tyr Cys Glu Gly Glu Cys Pro Ser His Ile Ala
            340                 345                 350

Gly Thr Ser Gly Ser Ser Leu Ser Phe His Ser Thr Val Ile Asn His
        355                 360                 365

Tyr Arg Met Arg Gly His Ser Pro Phe Ala Asn Leu Lys Ser Cys Cys
    370                 375                 380

Val Pro Thr Lys Leu Arg Pro Met Ser Met Leu Tyr Tyr Asp Asp Gly
385                 390                 395                 400

Gln Asn Ile Ile Lys Lys Asp Ile Gln Asn Met Ile Val Glu Glu Cys
                405                 410                 415

Gly Cys Ser


<210> SEQ ID NO 17
<211> LENGTH: 8
<212> TYPE: PRT
<213> ORGANISM: Artificial Sequence
<220> FEATURE:
<223> OTHER INFORMATION: Epitope tag

<400> SEQUENCE: 17

Asp Tyr Lys Asp Asp Asp Asp Lys
1               5
```